United States Patent
Oroskar et al.

(10) Patent No.: US 10,213,707 B2
(45) Date of Patent: Feb. 26, 2019

(54) CONTINUOUS PROCESS FOR PURIFICATION OF STEVIOL GLYCOSIDES FROM STEVIA LEAVES USING SIMULATED MOVING BED CHROMATOGRAPHY

(71) Applicant: Orochem Technologies, Inc., Naperville, IL (US)

(72) Inventors: Anil R. Oroskar, Oak Brook, IL (US); Babu Siddegowda Antharavally, Caledonia, IL (US); Pravin Ramkrishna Ninawe, Franklin, WI (US); Asha A. Oroskar, Oak Brook, IL (US); Xinjie Chen, Naperville, IL (US); Feng Peng, Chicago, IL (US); Rahuljit Pal, Willow Brook, IL (US)

(73) Assignee: Orochem Technologies, Inc., Naperville, IL (US)

( * ) Notice: Subject to any disclaimer, the term of this patent is extended or adjusted under 35 U.S.C. 154(b) by 244 days.

(21) Appl. No.: 15/375,040

(22) Filed: Dec. 9, 2016

(65) Prior Publication Data
US 2018/0161696 A1   Jun. 14, 2018

(51) Int. Cl.
| | | |
|---|---|---|
| A23L 5/20 | (2016.01) | |
| C07H 1/08 | (2006.01) | |
| A23L 27/30 | (2016.01) | |
| B01D 15/18 | (2006.01) | |
| B01D 15/36 | (2006.01) | |
| B01D 61/02 | (2006.01) | |
| B01D 61/14 | (2006.01) | |
| C07H 15/24 | (2006.01) | |

(52) U.S. Cl.
CPC .............. *B01D 15/185* (2013.01); *A23L 5/23* (2016.08); *A23L 27/33* (2016.08); *B01D 15/1842* (2013.01); *B01D 15/362* (2013.01); *B01D 15/363* (2013.01); *B01D 61/027* (2013.01); *B01D 61/147* (2013.01); *C07H 1/08* (2013.01); *C07H 15/24* (2013.01); *A23V 2002/00* (2013.01)

(58) Field of Classification Search
None
See application file for complete search history.

(56) References Cited

U.S. PATENT DOCUMENTS

| | | |
|---|---|---|
| 2,985,589 A | 5/1961 | Broughton |
| 6,228,966 B1 | 5/2001 | Zhou et al. |
| 9,169,285 B2 | 10/2015 | Prakash et al. |

(Continued)

OTHER PUBLICATIONS

Indra Prakash et al., "Development of Next Generation Stevia Sweetener: Rebaudioside M", Foods, 2014, vol. 3, pp. 162-175, MDPI AG, Basel, Switzerland.
Anonymous, "Steviol Glycosides",FAO JECFA Monographs 4 (2007).

*Primary Examiner* — Krishnan S Menon
*Assistant Examiner* — Bradley R Spies
(74) *Attorney, Agent, or Firm* — Leydig, Voit & Mayer, Ltd.

(57) ABSTRACT

Disclosed is a continuous process for the purification of steviol glycosides extracted from the dried stevia leaves using continuous simulated moving bed processes and nanofiltration without the addition of organic solvents to obtain a purified steviol product comprising sweet steviol glycosides. The sweet steviol glycosides can be used as substitutes for caloric sweeteners in beverages and in other food items.

20 Claims, 10 Drawing Sheets

(56) References Cited

U.S. PATENT DOCUMENTS

2011/0087011 A1* 4/2011 Chiang .................. C07H 1/08
 536/18.1
2014/0099403 A1* 4/2014 Prakash .................. A23L 2/60
 426/61

* cited by examiner

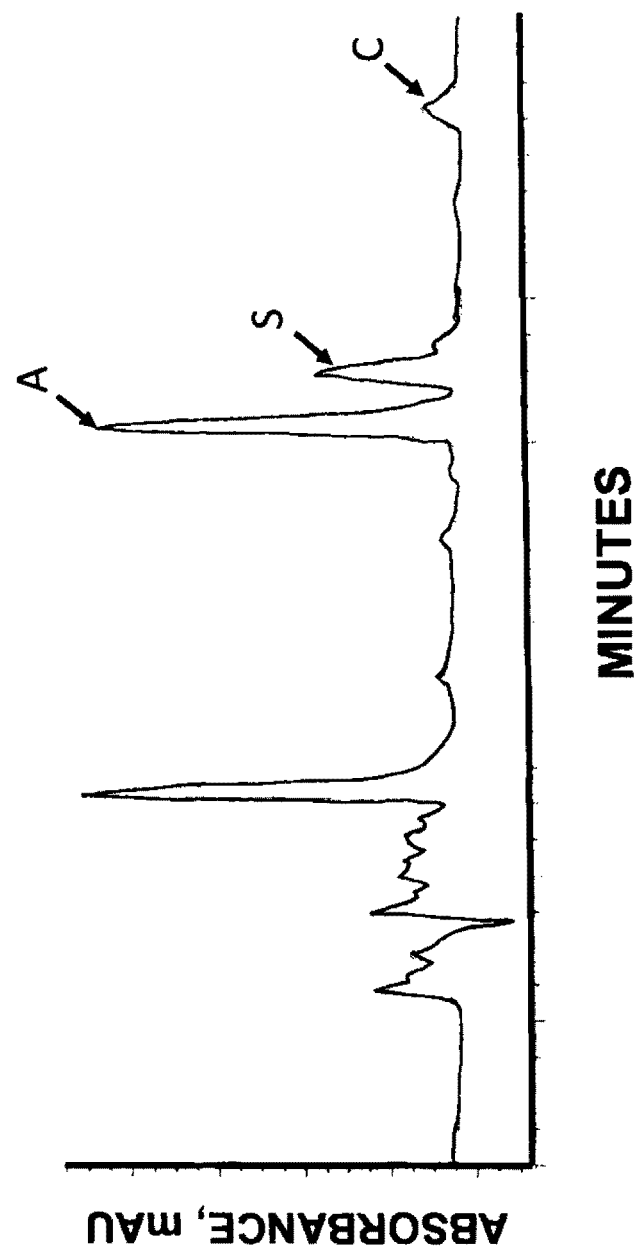

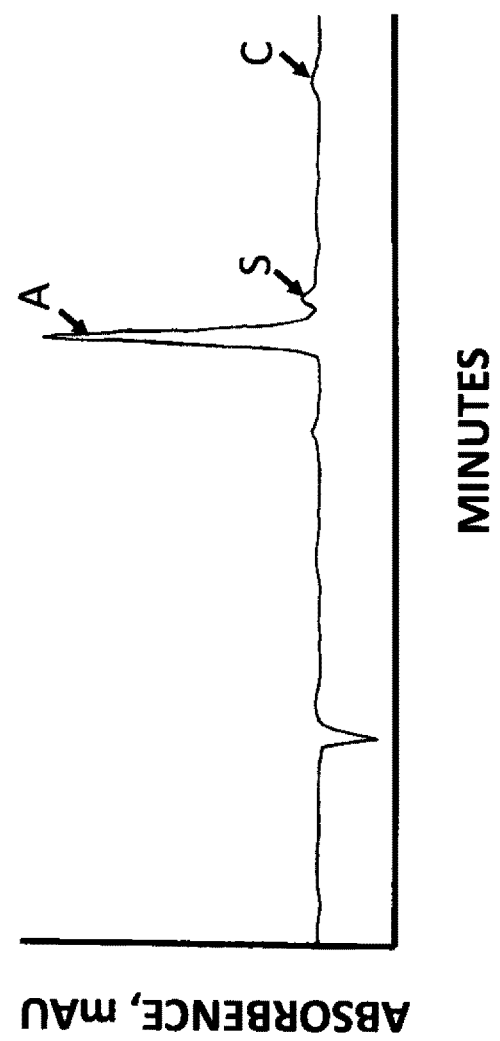

CONTINUOUS PROCESS FOR PURIFICATION OF STEVIOL GLYCOSIDES FROM STEVIA LEAVES USING SIMULATED MOVING BED CHROMATOGRAPHY

FIELD OF THE INVENTION

The invention relates to a method for purification and separation of steviol glycosides from dried *stevia* leaves and continuous purification of steviol glycosides. More particularly, the method relates to a process for the continuous purification of steviol glycosides extracted from the dried *stevia* leaves using simulated moving bed chromatography. Most particularly, the method relates to a novel continuous process for the purification of steviol glycosides extracted from the dried *stevia* leaves using a continuous simulated moving bed process using water exclusively as the mobile phase desorbent without the addition of organic solvents to obtain a purified steviol product comprising sweet steviol glycosides. The sweet steviol glycosides can be used as substitutes for caloric sweeteners in beverages and in other food items.

BACKGROUND

The worldwide demand for high potency sweeteners is increasing and, with blending of different sweeteners becoming a standard practice, the demand for alternatives is expected to increase. Such sweeteners include both caloric and low-caloric sweeteners. Caloric sweeteners include sucrose, fructose, and glucose. Recently, low-calorie (or non-calorie) sweeteners have gained increased popularity. These can be used as substitutes for caloric sweeteners and are often referred to as "sugar substitutes". Common sugar substitutes include saccharin, aspartame, and sucralose.

One such low-calorie sweetener is *stevia*, which is a sweetener derived from Steviol glycosides. Demand for Steviol glycosides is growing because of their non-toxic nature, their sugar-like taste profile, and their low caloric value, when used as sugar substitutes.

*Stevia rebaudiana Bertoni* is a perennial shrub of the *Asteraceae* (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10 to 20% of the total dry weight. These diterpene glycosides are about 150 to 450 times sweeter than sugar. Structurally, the diterpene glycosides are characterized by a single base, steviol, and differ by the presence of carbohydrate residues at positions $C13(R_2)$ and $C19(R_1)$. The structure of the steviol base is shown hereinbelow:

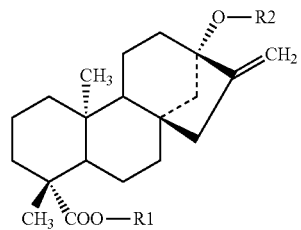

Table 1 illustrates the various steviol compounds with reference to the above steviol base.

TABLE 1

Chemical Structures of Steviol Glycosides

| Compound | R-Groups in Stevia Structure | | Formula | MW |
| --- | --- | --- | --- | --- |
| | $R_1$ | $R_2$ | | |
| Rebaudioside A | β-glc- | (β-glc)$_2$-β-glc- | $C_{44}H_{70}O_{23}$ | 967.01 |
| Rebaudioside B | H | (β-glc)$_2$-β-glc- | $C_{38}H_{60}O_{18}$ | 804.88 |
| Rebaudioside C | β-glc- | (β-glc,α-rha-)-β-glc | $C_{44}H_{70}O_{22}$ | 951.01 |
| Rebaudioside D | β-glc-β-glc- | (β-glc)$_2$-β-glc- | $C_{50}H_{80}O_{28}$ | 1129.15 |
| Rebaudioside E | β-glc-β-glc- | β-glc-β-glc- | $C_{44}H_{70}O_{23}$ | 967.01 |
| Rebaudioside F | β-glc- | (β-glc,β-xyl)-β-glc- | $C_{43}H_{68}O_{22}$ | 936.99 |
| Rebaudioside M | (β-glc)$_2$-β-glc- | (β-glc)$_2$-β-glc | $C_{56}H_{90}O_{33}$ | 1291.3 |
| Stevioside | β-glc- | β-glc-β-glc- | $C_{38}H_{60}O_{18}$ | 804.88 |
| Steviolbioside | H | β-glc-β-glc- | $C_{32}H_{50}O_{13}$ | 642.73 |
| Rubusoside | β-glc- | β-glc- | $C_{32}H_{50}O_{13}$ | 642.73 |
| Dulcoside A | β-glc- | α-rha-β-glc- | $C_{38}H_{60}O_{17}$ | 788.87 |

Glc—glucose;
rha—rhammose;
xyl—xylose

Typically, on a dry weight or anhydrous basis, the four major steviol glycosides found in the leaves of *stevia* are Dulcoside A (0.3%), Rebaudioside C (0.6-1.0%), Rebaudioside A (3.8%) and Stevioside (9.1%). Other steviol glycosides identified in *stevia* extract include Rebaudioside B, D, E, and F, Steviolbioside and Rubusoside. Among these, only Stevioside and Rebaudioside A are available on a commercial scale. Stevioside and Rebaudioside A are the component glycosides of principal interest for their sweetening property.

Steviol glycosides can be extracted from leaves using either water or organic solvent extraction. Typically, steviol glycosides are obtained from the leaves of *Stevia rebaudiana Bertoni*. The leaves are extracted with hot water and the resulting aqueous extract is passed through an adsorption resin to trap and concentrate the component steviol glycosides. Generally, the resin is desorbed by washing the resin with organic solvents like methanol or ethanol to release the glycosides. Typically, the steviol product is recrystallized with a solvent such as methanol or ethanol. Typically, the steviol product is recrystallized with a solvent such as methanol. Ion-exchange resins have been used in the purification process. The final product is typically spray-dried. (See *FAO JECFA Monographs* 4 (2007).

Supercritical fluid extraction and steam distillation methods have also been described. Methods for the recovery of diterpene sweet glycosides from *Stevia rebaudiana Bertoni* using supercritical $CO_2$, membrane technology, and water or organic solvents, such as methanol and ethanol, may also be used.

The wide use of steviol glycosides as sweeteners has been limited to date by the presence of certain undesirable taste properties, including licorice taste, bitterness, astringency, sweet aftertaste, bitter aftertaste, licorice aftertaste. The main sweetening component of *stevia* extract is rebaudioside A. Rebaudioside A provides the greatest degree of sweetening without the undesirable taste properties. Many of these undesirable taste properties can be minimized or eliminated by separating the steviol glycosides, particularly rebaudioside A from other rebaudioside isomers and other compounds associated with the plant extract. Such other compounds include: proteins, resins, organic acids, pigments and sesquiterpene lactones. The pigments include chlorophyll, xanthophyll and betacarotene.

Because the chemical structures of the steviol glycosides are very similar, obtaining a relatively pure form of rebaudioside A from the mixture of other isomers is a challenge. At present the published methods for purification of rebaudioside A typically require a cascade of process steps including: filtration, precipitation of undesired components, decolorization, anion and cation exchange, and multi-stage crystallization to provide a purity of 95 weight percent on a dry or anhydrous basis. Often these steps include at least four solvent changes, drying and resolving steps.

U.S. Pat. No. 6,228,996 discloses a method for purifying diterpene glycosides from plant sources wherein the plant components such as fruit, leaves, branches, and bark, etc., are extracted to obtain a liquid extract. The liquid extract is admixed with a saturated solution containing at least one metallic ion having a valence of 2 or 3 (preferably, $Al^{+++}$), and the resulting admixture is contacted with a resin to adsorb the diterpene glycosides of interest. The diterpene glycosides are desorbed from the resin by washing the resin with an alcohol solution to obtain an alcohol solution containing the diterpene glycosides. The alcohol solution is subsequently dried to provide a dry composition containing the diterpene glycosides.

U.S. Pat. No. 9,169,285 discloses methods for purifying steviol glycosides which include (a) passing a solution of steviol glycosides through a multi-column system including a plurality of columns packed with an adsorbent resin to provide at least one column having adsorbed steviol glycosides; (b) eluting the adsorbed fractions from the at least one column having adsorbed steviol glycosides using a desorbent being a solution comprising alcohol and water to provide an eluted alcoholic solution with high steviol glycoside content. Further processing steps include ion-exchange and decolorizing the eluted solution before solvent removal and drying steps to obtain a solid steviol glycoside product.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

Conventional methods for the purification of Steviol glycoside extracts are associated almost exclusively with the use of organic solvents, such as methanol, ethanol or ether. Typically, such methods require that the Steviol glycosides be initially absorbed on a resin, followed by elution of the adsorbed Steviol glycosides with an organic solvent. Thus concentrated, the resulting organic Steviol glycoside solutions are evaporated and further treated with an alcohol such as methanol or ethanol in a crystallization step to provide a purified, crystallized steviol glycoside product. To satisfy the growing demand for the *stevia* based sweeteners which meet commercial food quality requirements, there is a need for an efficient extraction process that can be carried out to produce the main sweetening components without the use of organic solvents. The potential for even small amounts of organic solvents remaining in the purified *stevia* glycoside product can be deleterious to human health.

SUMMARY

The process of the present invention relates to the purification of steviol glycosides directly from extracts of plant material in a process which uses novel chromatographic scheme. More specifically, Applicant has developed a sequence of purification steps and a novel simulated moving bed separation process (SMB) series of adsorbent/desorbent combinations and SMB configurations to bring about the enrichment and purification of steviol glycosides, particularly Rebaudioside A, stevioside and Rebaudioside C from extracts of the *stevia* plant such as, *Stevia rebaudiana Bertoni*, to provide a purified steviol glycoside product and without using any potentially toxic organic solvent. The simulated moving bed system employed is a combination of styrene-divinyl benzene copolymer, ion exchange and hydrophobic interaction based stationary phase adsorbents and a mobile phase comprising water in a combination of normal and reverse phase simulated moving bed separation zones to provide an enriched extract stream comprising major steviol glycosides (SG3): Rebaudioside A, Stevioside, and Rebaudioside C. A steviol glycoside product having a total steviol glycoside (TSG) purity greater than 95 wt percent (e.g., 96, 97, 98, 99, 99.5 wt-%) following evaporation or drying can be obtained.

In one embodiment, the invention is a continuous process for the purification of steviol glycosides from a crude steviol glycoside extract to provide a purified steviol glycoside product. The crude steviol glycoside extract comprises Rebaudioside A, Rebaudioside C, stevioside, other steviol glycosides, water, tri-terpenes, sterols, flavonoids, volatile oils, pigments, gums, proteins, carotenoids, chlorophyll, vitamins, phospholipids, saccharides, solid insolubles and salts. The process comprises:

a) passing the crude steviol glycoside extract to a first filtration zone comprising a microfiltration filter having a pore size of less than about 0.2 µm to remove at least a portion of the solid insolubles to provide a filtered steviol glycoside extract;

b) passing the filtered steviol glycoside extract and a first mobile phase desorbent stream consisting of water to a first swing bed simulated moving bed zone comprising a plurality of first swing adsorbent beds containing a hydrophobic resin selective adsorbent to adsorb Rebaudioside A, Rebaudioside C, stevioside, and other steviol glycosides to provide a first swing bed extract stream comprising Rebaudioside A, Rebaudioside C, stevioside, water, and other steviol glycosides and a first group of impurities including proteins, vitamins, phospholipids, saccharides, and salts, and to provide a primary first swing bed raffinate stream comprising Rebaudioside A, Rebaudioside C, stevioside, water, and other steviol glycosides and a secondary first swing bed raffinate comprising water, tri-terpenes, sterols, flavonoids, carotenoids chlorophyll, volatile oils, pigments, and gums and combining at least a portion of the primary first swing bed raffinate with the first swing bed extract stream wherein the hydrophobic resin selective adsorbent comprises an aromatic non-polar copolymer of styrene-divinyl benzene resin;

c) passing the first swing bed extract stream to a first nanofiltration zone to remove at least a portion of water from the first swing bed extract stream to provide a first nano retentate stream and a first nano permeate stream comprising water;

d) passing the first nano retentate stream and a second mobile phase desorbent comprising water to a second swing bed simulated moving bed zone comprising a plurality of second swing adsorbent beds which are disposed in pairs wherein a first second swing adsorbent bed in each pair contains a strongly acidic cation exchange resin and a second second swing adsorbent bed in each pair contains a weakly basic anion exchange resin, said plurality of second swing adsorbent beds in the second swing bed simulated moving bed zone being divided into an adsorption/desorption zone wherein each pair of second swing adsorbent beds is disposed in serial fluid communication and a regeneration zone wherein a first pair of second swing adsorbent beds is in serial communication and a second pair of second swing adsorbent beds comprise a regeneration zone cation bed and a regeneration zone anion bed, wherein the first nano retentate stream and a second mobile phase desorbent are intermittently passed to the adsorption/desorption zone to adsorb salts, pigment and proteins from the first nano retentate stream to provide a second swing bed elute stream comprising steviol glycosides, water, phospholipids, and saccharides, and on desorption with the second mobile phase desorbent provide a second swing bed raffinate stream comprising water, proteins, pigments and salts, and the regeneration zone comprises simultaneously passing a second swing bed water wash stream to the first pair of second swing adsorbent beds in the regeneration zone and simultaneously and sequentially passing a basic wash stream, the second swing bed water wash stream, an acid wash stream, and the second swing bed water wash stream to condition the regeneration zone cation bed, and simultaneously and sequentially passing the basic wash stream and the second swing bed water wash stream to condition the regeneration zone anion bed to regenerate the regeneration zone and provide a second swing bed waste water stream which is admixed with the second swing bed raffinate stream;

e) passing the second swing bed elute stream and a third mobile phase desorbent stream comprising water to a polishing bed simulated moving bed zone, said polishing bed simulated moving bed zone comprising a plurality of polishing bed adsorbent beds containing a hydrophobic interaction resin selective for first eluting a polishing zone total raffinate stream comprising saccharides and phospholipids, and to provide a polishing bed extract stream comprising steviol glycosides, said polishing bed extract stream comprising water and an enhanced amount of steviol glycosides relative to the amount of steviol glycosides in the crude steviol glycosides;

f) passing the polishing bed extract stream to a second nanofiltration zone to remove at least a portion of water from the polishing bed extract stream to provide a second nano retentate stream and a second nano permeate stream comprising water; and, g) passing the second nano retentate stream to a drying zone to remove the water and provide a solid steviol glycoside product comprising Rebaudioside A, Rebaudioside C and Stevioside and having a sweet steviol glycoside concentration greater than about 95% (w/w) on an anhydrous basis.

The purified product of the present invention comprises a sweet steviol glycoside concentration greater than about 98% (w/w) on an anhydrous basis.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 6 is a High Performance Liquid Chromatography (HPLC) chromatographic area plot showing the results of a composition analysis of the extract stream withdrawn from the First Swing Bed simulated moving bed zone of the present invention.

FIG. 7 is a High Performance Liquid Chromatography (HPLC) chromatographic area plot showing the results of a composition analysis of the second extract stream withdrawn from the Second Swing Bed simulated moving bed zone of the present invention.

FIG. 10 is a High Performance Liquid Chromatography (HPLC) chromatographic area plot showing the results of a composition analysis of an enriched polishing bed extract stream of the present invention.

DETAILED DESCRIPTION OF THE INVENTION

Figure 1:
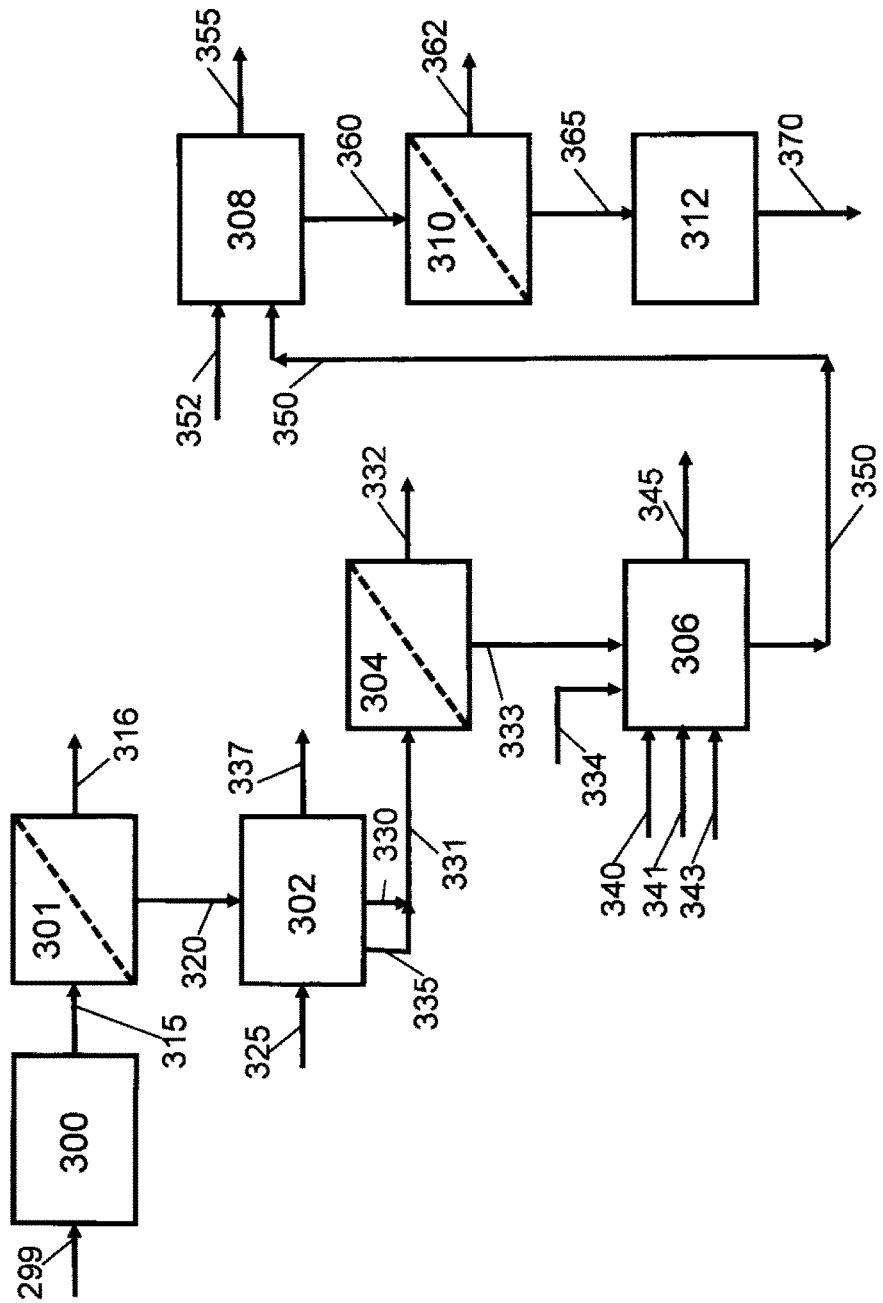
FIG. 1 is a schematic process flow diagram illustrating a configuration of the continuous overall process.

The sweet herb of Paraguay, *Stevia rebaudiana Bertoni*, produces an alternative sweetener with the added advantage that *stevia* sweeteners are natural plant products. The extract of the *Stevia rebaudiana Bertoni* plant contains a mixture of different sweet diterpene glycosides which have a single base, steviol, and differ by the presence of carbohydrate residues at positions C13 and C19. These steviol glycosides accumulate in *stevia* leaves and compose approximately 10%-20% of the total dry weight. Typically, on a dry weight basis, the four major glycosides found in the leaves of *stevia* are Dulcoside A (0.3%), Rebaudioside C (0.6-1.0%), Rebaudioside A (3.8%) and Stevioside (9.1%). Other steviol glycosides identified in *Stevia* extract include Rebaudioside B, D, E, F, M, N, O, KA, Steviolbioside and Rubusoside.

As used herein, the term "*stevia*" refers to the plant *stevia rebaudiana*, commonly known as sweetleaf, sweet leaf, sugarleaf, or simply *stevia* unless otherwise indicated. The phrase "*stevia* extract" refers to a sweetener-rich extract derived from the leaves of the *stevia rebaudiana* plant.

As used herein, the phrase "hot water" in the context of an extraction solvent refers generally to water having a temperature of 50° C. to 100° C.

As used herein, the term "steviol glycoside(s)" refers to glycosides of steviol, including, but not limited to, naturally occurring steviol glycosides, e.g. Rebaudioside A, Rebaudioside B, Rebaudioside C, Rebaudioside D, Rebaudioside E, Rebaudioside F, Stevioside, Steviolbioside, Dulcoside A, Rubusoside, etc. or synthetic steviol glycosides, e.g. enzymatically glucosylated steviol glycosides and combinations thereof.

As used herein, the term "sweet steviol glycosides" (SG3) is calculated as the sum of the content of three specific steviol glycosides on a dry (anhydrous) basis, including, Rebaudioside A (Reb A), Rebaudioside C (Reb C), and Stevioside (S).

As used herein, the term "other steviol glycosides" includes Rebaudioside D, Rebaudioside M, Rebaudioside F, Dulcoside A, Rebaudioside G, Rubusoside, Rebaudioside B and Steviolbioside.

As used herein, the term "total steviol glycosides" (TSG) is calculated as the sum of the content of all steviol glycosides on a dry (anhydrous) basis, including, for example, Rebaudioside A (Reb A), Rebaudioside B (Reb B), Rebaudioside C (Reb C), Rebaudioside D (Reb D), Rebaudioside E (Reb E), Rebaudioside F (Reb F), Rebaudioside G (Reb G), Rebaudioside M (Reb M), Stevioside, Steviolbioside, Dulcoside A and Rubusoside.

As used herein, the term "reversed-phase chromatography" employs a polar (aqueous) mobile phase. As a result, hydrophobic molecules in the polar mobile phase tend to adsorb to the hydrophobic stationary phase, and hydrophilic molecules in the mobile phase will pass through the column and are eluted first.

Applicant discovered a sequence of process operations for purifying the extract of the *stevia* plant which includes a micro filtration zone, first swing bed simulated moving bed zone, a first nanofiltration zone, second swing bed simulated moving bed zone, a polishing stage simulated moving bed zone, and a second nanofiltration zone provided a scheme wherein water could be employed exclusively as the mobile phase desorbent without requiring the addition of any organic solvent to provide a high purity steviol glycoside product.

The SMB system of the current invention was arranged for maximum selectivity. The simulated moving bed operation is achieved by use of a plurality of adsorbent beds connected in series or portions in series or parallel and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The SMB system may be operated such that the adsorbent beds are operated individually or in parallel using a single rotary valve and associated control system. A column may comprise one or several beds containing chromatographic media. Those feed tanks, filters, piping connecting flow between columns and/or beds where so connected, pumps, valving, pressure regulators, metering equipment, flow control and microprocessor equipment utilized in the embodiment are well known in construction and function to those of ordinary skill in the art.

Stationary Phase

The stationary phase adsorbent for use in the first swing bed simulated moving bed (SMB) chromatography zone is an aromatic non-polar copolymer of styrene-divinyl benzene adsorbent resin with an effective particle size of 0.25 mm and effective surface area of 590 m$^2$/g. Examples of suitable styrene-divinyl benzene adsorbent resins can be selected from the AMBERLITE XAD resin series (Available from Dow Chemical Company, Midland, Mich.), DIAION HP-20 (Available from Mitsubishi Chemical Company, Tokyo, Japan), or Stratosphere PL-PS/DVB (Available from Sigma-Aldrich, St. Louis, Mo.). The styrene-divinyl benzene adsorbent resin matrix provides an aromatic non-polar surface with selectivity for hydrophobic areas of molecules. In first swing bed simulated moving bed zone the steviol glycosides are retained on the resin and are subsequently recovered in a first swing bed extract stream. Impurities such as triterpenes, sterols, flavonoids and some of the pigments are rejected into a first swing bed raffinate stream. The stationary phase adsorbents may be disposed in a single adsorbent bed or may be disposed in within a single column or series of single columns containing multiple adsorbent bed zones.

In the second swing bed simulated moving bed (SMB) chromatography zone, two different adsorbents in series are employed to reject the steviol glycosides and retain impurities to provide a second swing bed extract stream comprising steviol glycosides and a second swing bed raffinate stream comprising impurities. The adsorbents are disposed in pairs of adsorbent columns or adsorbent beds which are in fluid communication and are connected in series, wherein the first adsorbent column or bed contains a strongly acidic cation exchange resin having an 8 percent cross-linkage with an effective particle size of about 0.5 mm and the second adsorbent column or bed contains a weakly basic anion exchange resin with an effective particle size of about 0.6 mm. The impurities removed in the second swing bed include ionic salts, metal ions, flavonoids, pigments, carotenoids, vitamins, and proteins, and in addition some color bodies are removed to at least partially decolorize first swing bed extract stream to provide the second swing bed extract having a second swing extract color ranging from light yellow to clear. In the second swing bed simulated moving bed zone, the impurities are retained on the resin and the steviol glycosides are rejected. Suitable examples of the strongly acidic cation exchange resin include: AMBERLITE IR-118 (Available from Dow Chemical Company, Midland, Mich.), or DIAION PK216LH (Available from Mitsubishi Chemical Company, Tokyo, Japan). Suitable examples of the weakly basic anion exchange resin include AMBERLITE IRA-70RF (Available from Dow Chemical Company, Midland, Mich.) or RELITE RAM2 (Available from Mitsubishi Chemical Company, Tokyo, Japan).

In the polishing bed simulated moving bed (SMB) zone, a porous hydrophobic interaction resin with a particle size of 70-200 microns is used to remove lipids and saccharides as impurities from the steviol glycosides. The lipid and saccharide impurities are rejected into a polishing bed raffinate stream and steviol glycosides are extracted into a polishing bed extract stream. Examples of suitable hydrophobic interaction resins having a particle size of about 70-200 microns include TOYOPEARL PHENYL-650C (Available from Tosoh Bioscience, Tokyo, Japan) or RELISORB PH400 (Available from Mitsubishi Chemical Company, Tokyo, Japan).

Mobile Phase Desorbent

The mobile phase desorbent of the present invention for use in all of the SMB zones for all adsorbents is water, preferably deionized water.

Feed Preparation

In the present invention, following harvesting and processing, the grinded and dried *stevia* leaves are extracted with an appropriate GRAS solvent or hot water. A number of different parameters can influence the overall yield, quality and/or purity of the desired final product. These parameters include, but are not limited to, the identity of the chosen GRAS solvent; the temperature and time at which the chosen natural solvent is used; the ratio of raw material to solvent (raw material:solvent (v/v)) that is employed; the number of successive extractions performed; the chosen method of purification of the desired products and the conditions related thereto. The skilled person will understand that these parameters are not necessarily mutually exclusive, and that a particular choice relating to one parameter may or may not affect the choice of other parameters. For example, the identity of the chosen natural solvent, and the temperature thereof, can affect the optimal ratio of raw material to solvent that is required to obtain the desired results. Following the extraction of the steviol glycosides from the *stevia* leaves, an extract stream comprising crude steviol glycosides is withdrawn from the extraction zone. Preferably, the crude steviol glycosides are admixed with water to provide a crude extract stream which comprises from about 34 wt-% to about 40 wt-% total steviol glycosides in the aqueous mixture. More preferably, the crude extract stream comprises from about 34 wt-% to about 37 wt-% total steviol glycosides in the aqueous mixture. The concentration of solids in the crude extract stream varies from about 60 to about 80 g/l and is preferably about 75 g/l.

The crude extract stream is passed to a microfiltration zone to remove any solid particles to provide a filtered extract stream. The microfiltration is carried at a microfiltration temperature ranging from about 50° C. to about 60° C. and the microfilter in the microfiltration zone ranges from about 0.2 µm to about 0.5 µm. Preferably, the microfilter pore size in the microfiltration zone comprises a microfilter pore size about 0.2 µm.

Nanofiltration is a membrane filtration-based method that uses nanometer sized cylindrical through-pores that pass through the membrane at 90°.

Nanofiltration membranes have pore sizes from 1-10 nanometers, smaller than that used in microfiltration and ultrafiltration, but just larger than that in reverse osmosis. Membranes used are predominantly created from polymer thin films. Materials that are commonly use include polyethylene terephthalate or metals such as aluminum. The nano filter pore size employed in the nanofiltration zones of present invention range from about 100 to 300 Da (Dalton). The pore size of a nanofiltration membrane in the nanofiltration zone characterized by a cut-off value. This cut-off value is consistent with the molecular weight of the smallest molecule that can be 90% restricted by the top layer of the membrane. The cut-off value of the nanofiltration membrane is typically expressed in Dalton (Dalton=weight in grams of mole of the molecule). More preferably, the pore size in the first nanofiltration zones is less than 150 Da. The nanofiltration is employed to remove excess water from extract streams withdrawn from simulated moving bed zones to obtain a target concentration of steviol glycosides in the effluent from the nanofiltration zone.

Detailed Description of the Drawings

Figure 2:
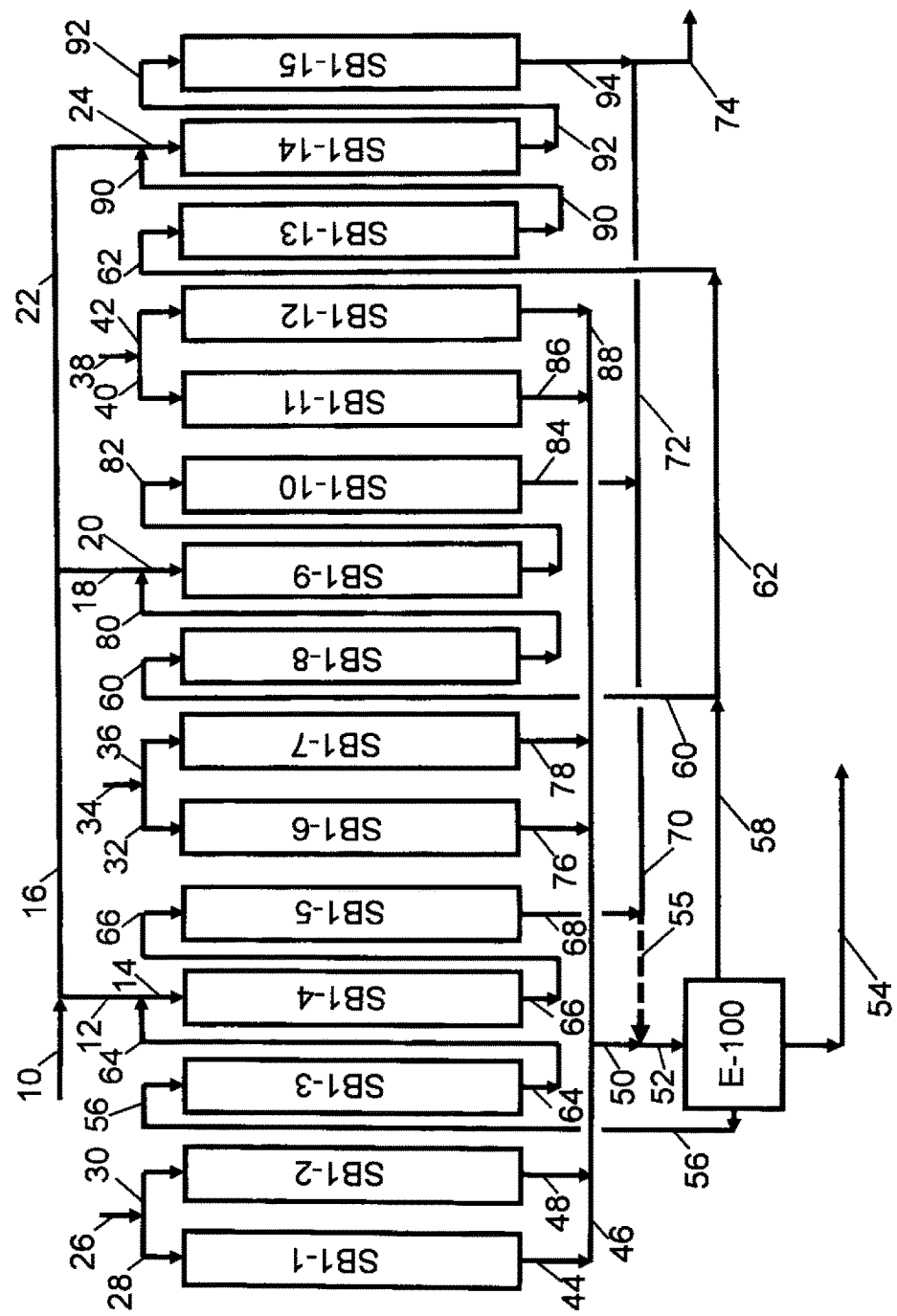
FIG. 2 is a schematic process flow diagram illustrating a configuration of the simulated moving bed cycle for a First Swing Bed simulated moving bed zone in one embodiment of the invention.

According to one embodiment of the invention and with reference to FIG. 1, dried *stevia* leaves from the *Stevia rebaudiana Bertoni*, plant are passed in line 299 to an extraction zone 300 and therein admixed with an effective amount of hot water (not shown) and agitated by conventional means to provide a crude steviol extract stream which is withdrawn in line 315. The crude steviol extract stream in line 315 is passed to a microfiltration zone 301 to remove at least a portion of solid particles and provide a filtered crude extract stream in line 320 and a first waste water stream in line 316. The microfiltration zone contains an extract filter which is a micro-filter having a 0.2 µm filter. Typically, the filtered crude extract stream comprises about 34-40 wt % total steviol glycosides on an anhydrous basis. The feed concentration of total steviol glycosides in the filtered extract stream comprises about 75 grams/liter. The filtered extract stream comprises sweet steviol glycosides (Rebaudioside A, Rebaudioside C, stevioside), other steviol glycosides, water, tri-terpenes, sterols, flavonoids, volatile oils, pigments, gums, proteins, carotenoids, chlorophyll, vitamins and saccharides, solid insolubles and salts. The overall process is continuous process along with nanofiltration units and water recovery plant. The process is carried out at a process operating temperature of the overall process ranging from about 50° C. to about 80° C. More preferably, the process is carried out at a process operating temperature of the overall process ranging from about 60° C. to about 80° C. Most preferably, the process is carried out at a process operating temperature which should not exceed 80° C. The desorbent used in the process is deionized water (DI water) having a pH of between about 6 and about 7, and having an electrical conductivity less than 5 µS/cm. The filtered crude extract stream in line 320 is passed to a first Swing Bed simulated moving bed zone 302 and the first waste water stream is passed to a waste water recovery zone (not shown). The first Swing Bed simulated moving bed zone 302 is further described hereinbelow in connection with FIG. 2. As shown in FIG. 2, the first Swing Bed simulated moving bed zone 302 consists of 15 first swing adsorbent beds, a rotary valve, an arrangement of valves and piping, and a valve control system. Each of the first swing adsorbent beds contain a first swing bed resin consisting of an aromatic, non-polar copolymer of styrene-divinyl benzene adsorbent resin. The first swing bed resin provides an aromatic non-polar surface with selectivity for hydrophobic areas of molecules for use in a simulated moving bed system based on hydrophobic interaction chromatography. In the first swing bed simulated moving bed zone, essentially all of the steviol glycosides are adsorbed on the first swing bed resin and impurities such as chlorophyll, sterols, volatile oils, tri-terpenes, volatile oils, carotenoids, vitamins and gum are rejected in aqueous first swing bed raffinate streams. The first swing bed mobile phase desorbent is water which is introduced in line 325 to provide a primary first Swing Bed raffinate stream in line 335, a secondary first Swing Bed raffinate stream in line 337, and a first Swing Bed extract stream in line 330. The primary first Swing Bed raffinate stream in line 335 is collected in the first half of each step of the first swing bed cycle, and the secondary first Swing Bed raffinate stream in line 337 is collected during the second or remaining portion of each step. The secondary first swing bed raffinate stream is essentially a waste stream which is continuously withdrawn and passed to a waste water recovery zone (not shown) comprising a reverse osmosis zone for recovery of water for use in the process. The primary first Swing Bed raffinate stream in line 335 and the first Swing Bed extract stream in line 330 are combined to provide the first swing bed extract stream in line 331. The first swing bed extract stream in line 331 is passed to a first nanofiltration zone 304, having a nano filter pore size of about 100 to 300 Da (Dalton), and wherein the first swing bed extract stream is concentrated to provide a first nano retentate stream in line 333 and a first nano permeate stream in line 332. The pore size of a nanofiltration membrane in the first nanofiltration zone 304 is characterized by a cut-off value. This cut-off value is consistent with the molecular weight of the smallest molecule that can be 90% restricted by the top layer of the membrane. The cut-off value of the nanofiltration membrane is typically expressed in Dalton (Dalton=weight in grams of mole of the molecule). More preferably, the pore size in the first nanofiltration zone 304 is less than 150 Da. The first nano permeate stream in line 332 is passed to the waste water recovery zone (not shown). The first nano retentate stream in line 333 and a second mobile phase desorbent stream comprising or consisting of water in line 334 are passed to a second swing bed simulated moving bed zone 306. The second Swing Bed simulated moving bed zone 306 is further described hereinbelow in connection with FIG. 3. The second swing Bed simulated moving bed zone 306 comprises a first series of second swing adsorbent beds which are serially connected adsorbent beds through which the first nano retentate stream in line 333 and the second mobile phase desorbent line 334 are passed, wherein during each of the steps of the second swing bed SMB cycle, at least one second swing adsorbent bed is charged or loaded with the first nano retentate stream for a portion of the step, after which the first series of serially connected second swing adsorbent beds are washed by passing the second mobile phase desorbent stream to wash the second swing adsorbent beds to provide a second swing bed elute stream in line 350 comprising water and essentially all of the steviol glycosides: Rebaudioside A, Rebaudioside C, and stevioside. The second series of second swing adsorbent beds are separately washed in isolation by introducing an acid wash stream in line 340, a basic wash stream in line 341, and a water wash stream in line 343 to regenerate the second swing adsorbent beds and to provide a second swing bed raffinate stream in line 345. The second swing bed raffinate stream in line 345 comprises waste water which is passed to the water recovery zone (not shown) for water recovery. The second swing bed extract stream in line 350 and a polishing bed mobile phase desorbent stream in line 352 consisting or containing water are passed to a polishing bed zone 308. The polishing bed zone 308 comprises a series of polishing bed adsorbent beds operated as a simulated moving bed system, and include at least 15 polishing bed adsorbent beds, a valve control system, a rotary valve, and associated piping. The polishing bed zone 308 is further described hereinbelow in connection with FIG. 4. In one embodiment, the polishing bed adsorbent beds are divided into at least two sections. The first section and the second section each comprise three zones. The polishing bed zone provides a polishing bed extract stream in line 360 and a polishing zone total raffinate stream in line 355. The polishing zone total raffinate stream in line 355 is passed to the waste water recovery zone (not shown) for recovery of water for use in the process. The polishing bed extract stream in line 360 is passed to a second nanofiltration zone 310 to provide a filtered polished extract stream in line 365 and a second nano permeate stream in line 362. The pore size of the nanofiltration membrane in the second nanofiltration zone 310 is characterized by a cut-off value of 100 to 300 Da. More preferably, the pore size of the nanofiltration membrane in the second nanofiltration zone 310 is less than 150 Da. The filtered polished extract stream in line 362 is passed to a spray drying zone 312 to remove water in a conventional manner and provide a dry *stevia* product in line 370 comprising essentially sweet *stevia* glycosides (SG3). The dry *stevia* product comprised an SG3 concentration ranging from 92 to 95 wt-% on an anhydrous basis. More preferably, the dry *stevia* product comprises an SG3 concentration greater than or equal to 95 wt-% on an anhydrous basis. The dry *stevia* product may be in the form of powder, aggregates or pellets.

According to one embodiment of the invention and with reference to FIG. 2, the first swing bed simulated moving bed system (SB1) is a continuous simulated moving bed system which continuously processes the filtered crude extract stream in line 10 to provide a first swing bed elute stream in line 54. The first swing bed simulated moving bed system (SB1) comprises a plurality of first swing adsorbent beds wherein the plurality of first swing adsorbent beds are separated into at least three identical sections which are operated in parallel, and each section comprises three zones. Each adsorbent bed has a top and a bottom and each first swing adsorbent bed contains a selective adsorbent being a non-polar copolymer styrene-divinylbenzene adsorbent resin and being a spherical particle with a 0.5 mm diameter. An example of such a non-polar resin is DIAION™ HP-20 (Available from Mitsubishi Chemical Corporation, Japan). With reference to FIG. 2, adsorbent beds SB1-1 through SB1-5 comprise the first SB1 section, first swing adsorbent beds SB1-6 through SB1-10 comprise the second SB1 section, and SB1-11 through SB1-15 comprise the third SB1 section. Within the first SB1 section, the first mobile phase desorbent comprising or consisting of deionized water in line 26 is passed to the top of zone 1 of section 1 (adsorbent beds SB1-1 and SB1-2) via line 26 and lines 28 and 30 to the top of adsorbent beds SB1-1 and SB1-2, respectively. In section 1, zone 1, the mobile phase desorbent is passed to the top of first swing adsorbent beds SB1-1 and SB1-2 via lines 28 and 30, respectively, to provide a first swing bed elute, which is withdrawn from the bottom of first swing adsorbent beds SB1-1 and SB1-2 in lines 44 and 48, respectively, and passed via elute header 46 to a first swing bed elute surge tank E-100 via lines 50 and 52. In zone 2 of section 1, a portion of the first swing bed elute is withdrawn from first swing bed elute surge tank E-100 via line 56 and passed to the top of zone 2 of section 1 or first swing adsorbent bed SB1-3 and the effluent of first swing adsorbent bed SB1-3 is passed via line 64 to be admixed with a portion of the filtered extract stream which is introduced via line 10 and lines 12, and the admixture passed via line 14 to the top of zone 3 of section 1. In zone 3 of section 1, first swing adsorbent beds SB1-4 and SB1-5 are arranged in serial fluid communication, whereby the effluent from the bottom of first swing adsorbent bed SB1-4, an extract recycle stream, is passed to the top of first swing adsorbent bed SB1-5 in line 66, and a first swing bed raffinate stream is withdrawn from the bottom of adsorbent bed SB1-5 via line 68. During each step of the first swing bed SMB cycle, for the first portion of the step, a first portion of the first swing bed raffinate stream in line 68 is passed via lines 68, 55 and 52 to be admixed with the first swing bed elute in the first swing bed elute surge tank E-100. In the second or remaining portion of each step of the first swing bed SMB cycle, a secondary swing bed raffinate is withdrawn from SB1-5 as a first swing bed secondary raffinate stream and passed via lines 68, 70, 72, and 74 to provide a net first swing bed secondary raffinate stream in line 74 which is a waste water stream and may be passed to waste water recovery (not shown). Similarly, in the second SB1 section, first mobile phase desorbent comprising or consisting of deionized water in line 34 is passed to zone 1 of section 2 via line 34. In section 2, zone 1, the first mobile phase desorbent is passed to the top of adsorbent beds SB1-6 and SB1-7 via lines 32 and 36, respectively, to provide first swing bed elute, which is withdrawn for the bottom of adsorbent beds SB1-6 and SB1-7 in lines 76 and 78, respectively, and passed via elute header 46 to the first swing bed elute surge tank E-100 via lines 50 and 52. In zone 2 of section 2, a portion of the first swing bed elute is withdrawn from first swing bed elute surge tank E-100 via lines 58 and 60 and passed to the top of zone 2 of section 2 or adsorbent bed SB1-8, and the effluent of adsorbent bed SB1-8 is passed via line 80 to be admixed with a portion of the filtered extract stream which is introduced via line 10, 16 and line 18, and the admixture passed via line 20 to the top of zone 3 of section 2. In zone 3 of section 2, first swing adsorbent beds SB1-9 and SB1-10 are arranged in serial fluid communication whereby the effluent from the bottom of first swing adsorbent bed SB1-9 is passed to the top of first swing adsorbent bed SB1-10 in line 82, and the first swing bed raffinate stream is withdrawn from the bottom of first swing adsorbent bed SB1-10 via line 84. During each step of the first swing bed SMB cycle, for the first portion of each step, the first portion of the first swing bed primary raffinate stream in line 84 is passed via lines 84, 70, 55 and 52 to be admixed with the first swing bed elute in the first swing bed elute surge tank E-100. In the second or remaining portion of each of the first swing bed steps, the secondary swing bed raffinate is withdrawn from first swing adsorbent bed SB1-10 as a first swing bed secondary raffinate stream and passed via lines 84, 72, and 74 to provide net first swing bed secondary raffinate stream in line 74 which is an SB1 waste water stream and may be passed to waste water recovery (not shown). Similarly, in the third SB1 section, first mobile phase desorbent comprising or consisting of deionized water in line 38 is passed to zone 1 of section 3 via line 38. In section 3, zone 1, the first mobile phase desorbent is passed to the top of first swing adsorbent beds SB1-11 and SB1-12 via lines 40 and 42, respectively, to provide a first swing bed elute, which is withdrawn for the bottom of first swing adsorbent beds SB1-11 and SB1-12 in lines 86 and 88, respectively, and passed via elute header 46 to a first swing bed elute surge tank E-100 via lines 50 and 52. In zone 3 of section 1, a portion of the first swing bed elute is withdrawn from first swing bed elute surge tank E-100 via lines 58 and 62, and passed to the top of zone 2 of section 3 or first swing adsorbent bed SB1-13 and the effluent of adsorbent bed SB1-13 is passed via line 90 to be admixed with a portion of the filtered extract stream which is introduced via lines 10, 16 and 22, and the admixture passed via line 24 to the top of first swing adsorbent bed SB1-14 in zone 3 of section 3. In zone 3 of section 3, first swing adsorbent beds SB1-14 and SB1-15 are arranged in serial fluid communication, whereby the effluent from the bottom of first swing adsorbent bed SB1-14 is passed to the top of first swing adsorbent bed SB1-15 in line 92, and the first swing bed raffinate stream is withdrawn from the bottom of first swing adsorbent bed SB1-15 via line 94 and passed to the first swing bed secondary raffinate header (line 74). During each step of the first swing bed SMB cycle, for the first portion of each step of the first swing bed SMB cycle, a portion of the first swing bed raffinate stream in line 94 is passed via lines 94, 72, 70, 55 and 52 to be admixed with the first swing bed elute in the first swing bed elute surge tank E-100. In the second or remaining portion of each of the steps the first swing bed SMB cycle, the secondary swing bed raffinate is withdrawn from first swing adsorbent bed SB1-15 as a first swing bed secondary raffinate stream and passed via lines 94 and 74 to provide a portion of the first swing bed secondary raffinate stream in line 74 which is a waste water stream and may be passed to waste water recovery (not shown). At the completion of each of the steps of the first swing bed SMB cycle, the rotary valve is sequenced to increment each first swing adsorbent bed by one position to the left in a counterclockwise manner, whereby SB1-15 is moved to the position of SB1-14, and so on, and SB1-1 is moved to the position previously occupied by SB1-15.

In one embodiment, the first swing bed simulated moving bed zone has a plurality of first swing adsorbent beds which are disposed in one or more clockwise, sequentially disposed sections. Each section comprises five first swing adsorbent beds and separated into 3 zones, wherein a zone 1 comprises the first two first swing adsorbent beds which are desorbed with a portion of the first mobile phase desorbent to provide a portion of the first swing extract stream, a zone 2 comprising the third first swing adsorbent bed, which is loaded with a portion of the first mobile phase desorbent to provide a portion of an extract recycle stream. The portion of an extract recycle stream is admixed with the filtered crude extract stream and passed to the fourth and fifth first swing adsorbent beds to load the first swing adsorbent and to provide a portion of the primary first swing bed raffinate stream during a first portion of a simulated moving bed step and a portion of the secondary first swing bed raffinate stream during a second or remaining portion of a simulated moving bed step. At the completion of each of the steps of the first swing bed SMB cycle, a rotary valve is sequenced to increment each first swing adsorbent bed by one position to the left in a counterclockwise manner.

Figure 3:
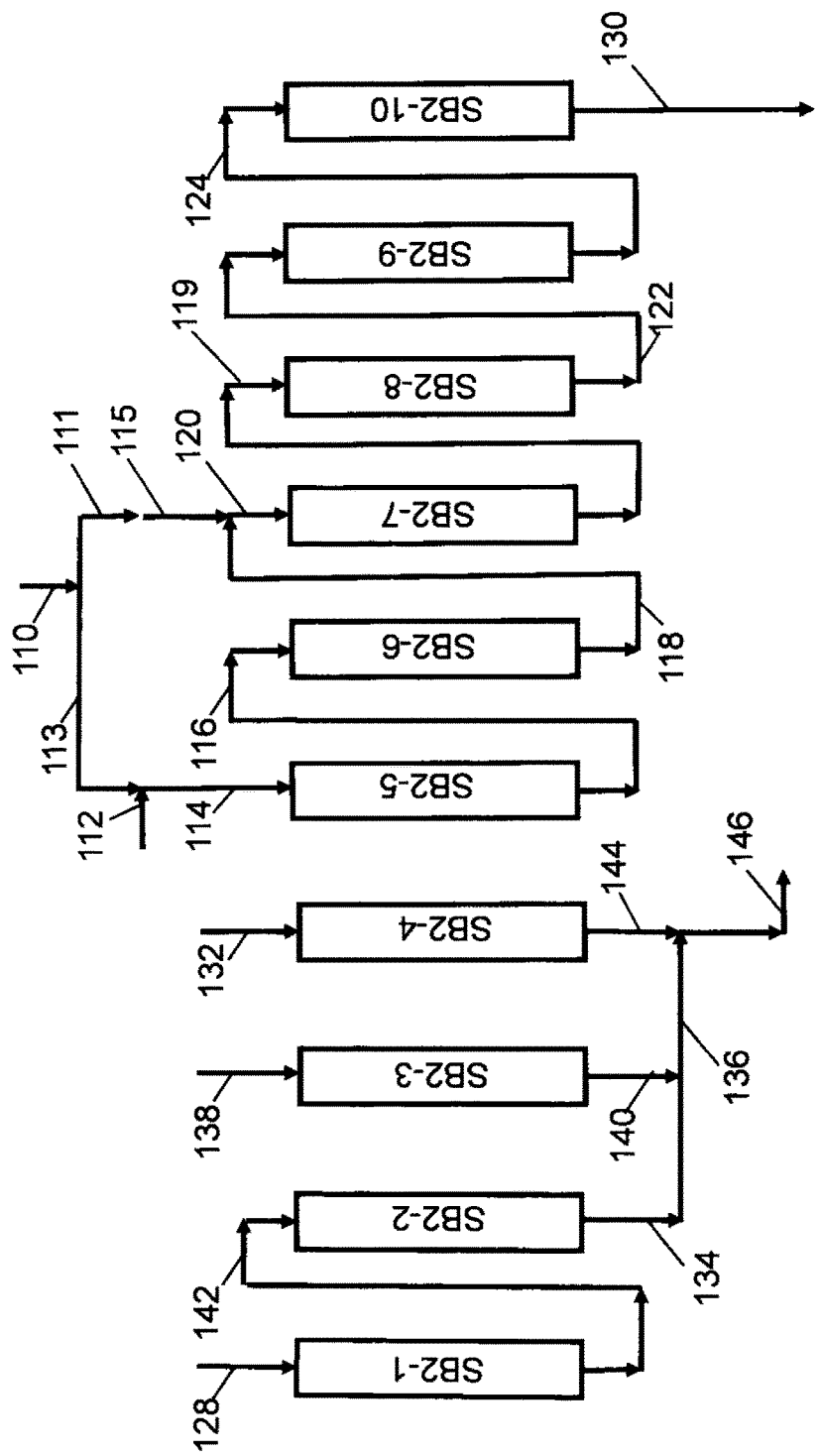
FIG. 3 is a schematic process flow diagram illustrating a configuration of the simulated moving bed cycle for a Second Swing Bed simulated moving bed zone in one embodiment of the invention.

According to one embodiment of the invention and with reference to FIG. 3, the second swing bed simulated moving bed system is a continuous simulated moving bed system which continuously processes the first swing bed elute stream after nanofiltration, or first nano retentate stream, in line 110 and a second mobile phase desorbent stream in line 112 to provide a second swing bed elute stream in line 130. The second swing bed simulated moving bed system (SB2) comprises a plurality of second swing adsorbent beds wherein the plurality of second swing adsorbent beds are separated into an adsorption/desorption section (SB2-5-SB2-10) and a regeneration section (SB2-1-SB2-4). As shown in FIG. 3, second swing adsorbent beds SB2-5 through SB2-10 represent the adsorption/desorption zone of the second swing bed simulated moving bed system (SB2) wherein second swing adsorbent beds SB2-5 through SB2-10 are second swing adsorbent beds and contain a selective adsorbent as described hereinabove and each second swing adsorbent bed has a top and a bottom. In one embodiment, the second swing adsorbent beds alternately contain either a strongly acidic cation exchange resin or a weakly basic anion exchange resin. For example, the odd numbered adsorbent beds (SB2-1, SB2-3, SB2-5, SB2-7, and SB2-9) contain a strongly acidic cation exchange resin and the even numbered adsorbent beds (SB2-2, SB2-4, SB2-6, SB2-8, and SB2-10) contain a weakly basic anion exchange resin. In the adsorption/desorption zone, second swing adsorbent beds SB2-5 through SB2-10 are in serial fluid communication wherein the effluent of SB2-5 is passed from the bottom of second swing adsorbent bed SB2-5 to the top of second swing adsorbent bed SB2-6 via line 116; the effluent of second swing adsorbent bed SB2-6 is passed from the bottom of second swing adsorbent bed SB2-6 to the top of second swing adsorbent bed SB2-7 via lines 118 and 120; the effluent of SB2-7 is passed from the bottom of second swing adsorbent bed SB2-7 to the top of second swing adsorbent bed SB2-8 via line 119; the effluent of second swing adsorbent bed SB2-8 is passed from the bottom of second swing adsorbent bed SB2-8 to the top of second swing adsorbent bed SB2-9 via line 122; and, the effluent of SB2-9 is passed from the bottom of second swing adsorbent bed SB2-9 to the top of second swing adsorbent bed SB2-10 via line 124. The second swing bed elute stream in line 130 is withdrawn from the bottom of second swing adsorbent bed SB2-10. The second swing bed elute stream comprises steviol glycosides and is essentially free of ionic impurities such as salts and proteins. By the term essentially free of ionic impurities the second swing bed elute stream contains less than about 0.5 wt-% ionic impurities on an anhydrous basis.

During each step of the second swing bed SMB cycle, the nanofiltered elute stream in line 110 is introduced to SB2-5 via lines 110, 113 and 114 and to SB2-7 via lines 110, 111, and 115 and 120 for a portion of each step in a loading step, after which for the remainder of each step, the adsorbent beds (SB2-5-SB2-10) are serially and sequentially washed with the second mobile phase desorbent comprising or consisting of water introduced in lines 112 and 114 to adsorbent bed SB2-5 to provide a second swing bed extract stream in line 130. The SB2 regeneration section (SB2-1-SB2-4) operates essentially in parallel carrying out a series of regeneration steps which include:

(1) a serial water wash zone wherein a adsorbent beds SB2-1 (cation) and SB2-2 (anion) pair of adsorbent beds are water washed by passing a second water wash stream in line 128 to the top of adsorbent bed SB2-1, withdrawing the wash effluent from adsorbent bed SB2-1 in line 142 and passing the wash effluent to the top of adsorbent bed SB2-2 and withdrawing a first SB2 waste water stream I line 134;

(2) a basic/acidic regeneration zone wherein adsorbent bed SB2-3, containing the strongly acidic cation adsorbent is subjected to a four part regeneration procedure wherein (a) adsorbent bed SB2-3 is washed with an aqueous basic solution such as sodium hydroxide having an NaOH concentration of from about 2 grams/100 ml water to about 4 grams/100 ml water NaOH (a NaOH concentration ranging from a 0.5N to 1N NaOH solution), (b) washed with a water wash stream in a first regeneration wash step, (c) washed with an aqueous mild acid solution such as HCl having an HCl concentration of from about 2 ml HCl per 100 ml water to about 4 ml HCl per 100 ml water (an HCl concentration of from 0.2 to 0.6 N HCl solution) to reactivate the adsorbent, and (d) washed in a second water wash with the water wash stream; and (3) an basic regeneration zone wherein adsorbent bed SB2-4, containing the weakly basic anion adsorbent is subjected to a two part regeneration procedure wherein (a) adsorbent bed SB2-4 is washed with an aqueous basic solution such as sodium hydroxide having an NaOH concentration of from about 2 grams/100 ml water to about 4 grams/100 ml water NaOH (a NaOH concentration ranging from a 0.5N to 1N NaOH solution), and (b) washed in a second water wash with the water wash stream.

All of the parts of the above series of four part regeneration streams are introduced to adsorbent bed SB2-3 sequentially in line 138 and a regeneration zone effluent stream is withdrawn in line 140 as a second SB2 waste water stream. Second swing adsorbent bed SB2-4 is sequentially washed by passing a basic solution via line 132 to the top of second swing adsorbent bed SB2-4, followed by washing the second swing bed adsorbent bed SB-2-4 with a water wash stream introduced in line 132 to provide a third SB2 waste water stream line 144. The basic solution in line 132 is an aqueous basic solution wherein the base is an alkali metal such as sodium, and the base is sodium hydroxide having a concentration ranging between about 2 grams/100 ml water to about 4 grams/100 ml water (a NaOH concentration ranging from a 0.5N to 1N NaOH solution). The first waste water stream in line 134, the second SB2 waste water stream in line 140, and the third waste water stream in line 144 are collected in line 146 as a total SB2 waste water stream and passed to the waste water recovery zone (not shown). In the operation of the second swing bed simulated moving bed system (SB2), the second swing adsorbent beds are moved in cation/anion pairs. Thus, at the completion of each step of the second swing bed SMB cycle, the rotary valve is sequenced to increment each second swing adsorbent bed by two positions (n+2) to the left in a counterclockwise manner, whereby second swing adsorbent beds SB2-3 and SB2-4 are moved to the position of second swing adsorbent beds SB2-1 and SB2-2, and so on; and second swing adsorbent beds SB2-1 and SB2-2 are moved to the positions previously occupied by second swing adsorbent beds SB2-9 and SB2-10.

Figure 4:
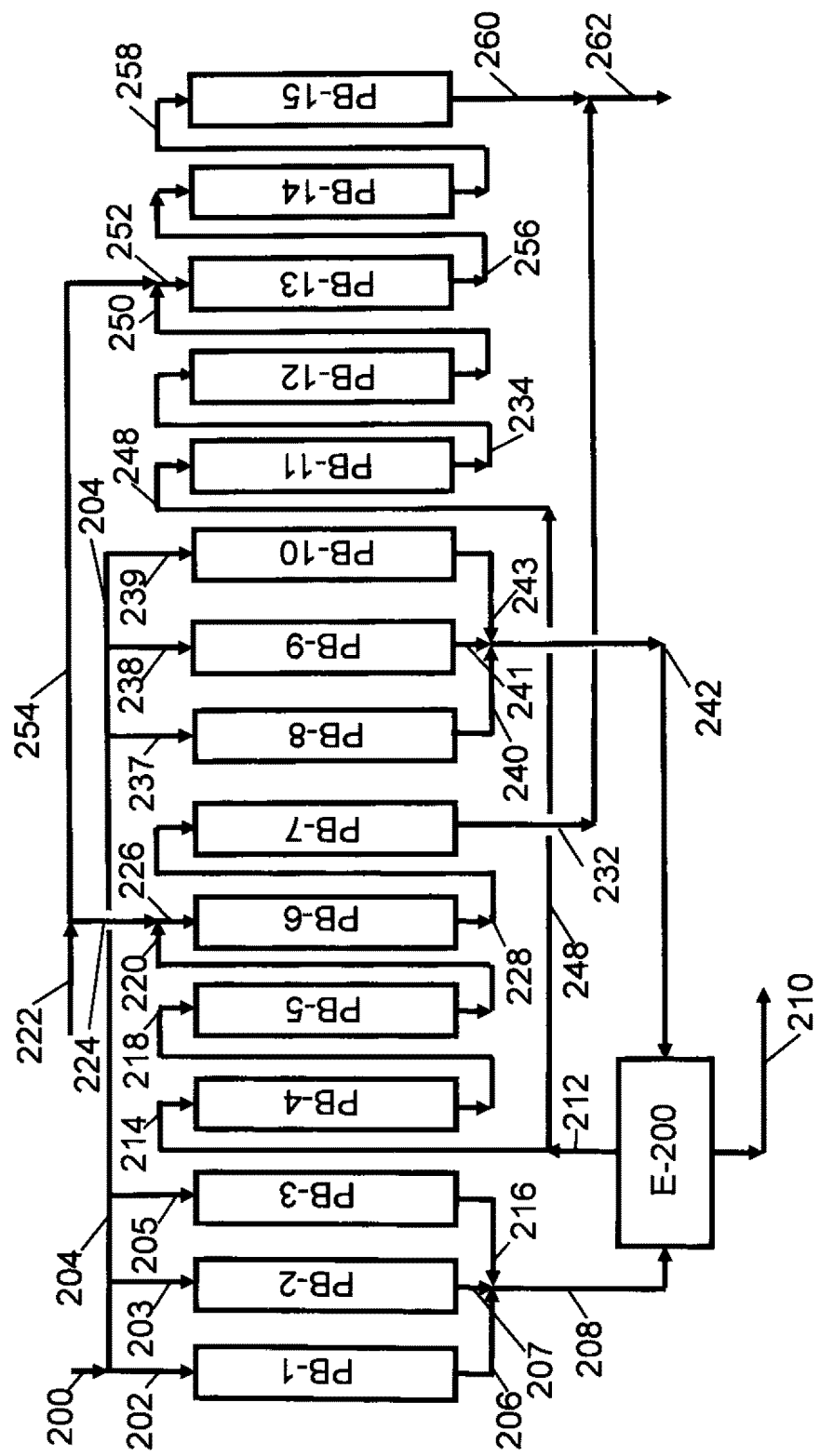
FIG. 4 is a schematic process flow diagram illustrating a configuration of the simulated moving bed cycle for a Polishing Bed simulated moving bed zone in one embodiment of the invention.

According to one embodiment of the invention and with reference to FIG. 4, the polishing bed simulated moving bed system is a continuous simulated moving bed system which continuously processes the second swing bed extract stream in line 222 to provide a polishing bed extract stream or purified steviol glycoside stream in line 210. With reference to FIG. 4, the polishing bed simulated moving bed system comprises a plurality of polishing bed adsorbent beds containing a selective adsorbent. Each of the polishing bed adsorbent beds has a top and a bottom. The polishing bed adsorbent beds may be sequentially disposed linearly or sequentially disposed about a circumference of a circle. The plurality of polishing bed adsorbent beds are separated or grouped into at least two identical sections which are operated in parallel. The polishing bed simulated moving bed zone is shown with 15 polishing bed adsorbent beds (PB-1 to PB-15), wherein the first section, or section A includes polishing bed adsorbent beds PB-1, PB-2, PB-3, PB-4, PB-5, PB-6, and PB-7, and a second section, section B includes polishing bed adsorbent beds PB-8, PB-9, PB-10, PB-11, PB-12, PB-13, PB-14 and PB-15. Each Section contains 3 zones (1, 2, and 3). The first PB zone, zone 1, is a desorption zone wherein upon introduction of desorbent, an extract is removed. The second PB zone, zone 2 is a separation zone, wherein steviol glycosides are adsorbed and separated from fatty acids, saccharides, and phospholipids. In the third PB zone, zone 3, or loading zone, the second swing bed extract is loaded on to the polishing bed adsorbent beds in zone 3 and the polishing bed raffinate is withdrawn. The polishing bed is typically configured with one or more sections wherein each polishing bed zone has at least two polishing bed adsorbent beds, and each section has a 3-2-2 arrangement having 3 polishing bed adsorbent beds in the desorption zone, 2 polishing bed adsorbent beds in the separation zone, and 2 polishing bed adsorbent beds in the loading zone, or a 3-2-3 arrangement having 3 polishing bed adsorbent beds in the desorption zone, 2 polishing bed adsorbent beds in the separation zone, and 3 polishing bed adsorbent beds in the loading zone. Preferably there are at least two or more polishing bed adsorbent beds in the loading zone. Thus a polishing bed SMB system having one section could include 7 or 8 polishing bed adsorbent beds, having two sections could include 14 or 15 polishing bed adsorbent beds, or having three sections could include 21-24 polishing bed adsorbent beds. The desorbent is introduced to the top of zone 1 wherein the desorbent contacts the hydrophobic adsorbent and extract is withdrawn from zone 1. A portion of the extract is recycled to zone 2, and the effluent of zone 2 is admixed with the elute stream from the second swing bed simulated moving bed system (SB2) before being passed to zone 3. The effluent from zone 3 is raffinate. Referring to FIG. 4, the third mobile phase desorbent stream comprising or consisting of deionized water in line 200 is passed to the top of zone 1 of section A which comprises polishing bed adsorbent beds PB-1, PB-2, and PB-3 that are arranged in parallel, wherein the mobile phase desorbent is simultaneously introduced to the top of polishing bed adsorbent bed PB-1 via line 200 and 202, to the top of adsorbent bed PB-2 via lines 200, 204 and 203, and top of polishing bed adsorbent bed PB-3 via lines 200, 204 and 205 to provide a zone 1 effluent stream from adsorbent bed PB-1, which is withdrawn from the bottom of polishing bed adsorbent bed PB-1 in line 206, from polishing bed adsorbent bed PB-2 which is withdrawn from the bottom of polishing bed adsorbent bed PB-2 in line 207, and from polishing bed adsorbent bed PB-3 which is withdrawn from the bottom of polishing bed adsorbent bed PB-3 in line 216, and passed as a section A extract stream to a polishing bed extract surge tank E-200 in line 208 to provide a pooled extract stream in the extract surge tank E-200. At least a portion of the pooled extract stream from the polishing bed extract surge tank E-200 is withdrawn via lines 212 and 214 and passed to the top of section A zone 2 comprising polishing bed adsorbent beds PB-4 and PB-5. Polishing bed adsorbent beds PB-4 and PB-5 are arranged in serial fluid communication wherein the at least a portion of the section A extract stream is introduced to the top of polishing bed adsorbent bed PB-4 via line 214 and a first zone 2 effluent from adsorbent bed PB-4 is withdrawn from the bottom of polishing bed adsorbent bed PB-4 and passed in line 218 to the top of polishing bed adsorbent bed PB-5. A second section A zone 2 effluent stream in line 220 is withdrawn from the bottom of polishing bed adsorbent bed PB-5 as the Section A zone 2 effluent stream in line 220 and passed to the top of section A zone 3 which comprises polishing bed adsorbent beds PB-6 and PB-7. The Section A zone 2 effluent stream in line 220 is admixed with a second swing bed extract stream, or polishing bed zone feed stream introduced via lines 222 and 224 to provide a feed mixture in line 226 which is passed to the top of section A, zone 3. Section A zone 3 comprises polishing bed adsorbent beds PB-6 and PB-7 which are in serial fluid communication wherein the polishing bed feed stream is passed to the top of polishing bed adsorbent bed PB-6 in line 226 and an intermediate section A zone 3 stream is withdrawn from the bottom of polishing bed adsorbent bed PB-6 in line 228 and passed to the top of polishing bed adsorbent bed PB-7 and the effluent from polishing bed adsorbent bed PB-7 or the first section polishing bed raffinate stream in line 232 is withdrawn from polishing bed adsorbent bed PB-7 as a portion of the total polishing bed raffinate stream in line 262. The polishing bed raffinate stream is considered a waste water stream and is passed to waste water treatment for recovery of water. The mobile phase desorbent mixture in line 200 is passed to the top of zone 1 of section B via mobile phase desorbent header 204 and lines 237, 238 and 239 to polishing bed adsorbent beds PB-8, PB-9 and PB-10, respectively. Polishing bed adsorbent beds PB-8, PB-9 and PB-10 make up zone 1 of section B and are arranged in parallel whereby the mobile phase desorbent is introduced to the top of polishing bed adsorbent beds PB-8, PB-9 and PB-10 to provide a section B zone 1 effluent stream which is withdrawn from the bottom of polishing bed adsorbent beds PB-8, PB-9 and PB-10, in lines 240, 241, and 243, respectively, and which are combined in line 242 and passed to the polishing bed extract surge tank E-200 to provide the pooled extract stream in the extract surge tank E-200. At least a portion of the section B extract stream is passed to the top of section B zone 2 via lines 212 and 248. Section B zone 2 comprises polishing bed adsorbent beds PB-11 and PB-12 which are in serial fluid communication. A section B zone 2 intermediate stream is withdrawn from the bottom of polishing bed adsorbent bed PB-11 and passed to the top of polishing bed adsorbent bed PB-12 via line 234 to provide a section B zone 2 effluent stream in line 250 which is withdrawn from the bottom of polishing bed adsorbent bed PB-12 and passed to the top of section B zone 3, polishing bed adsorbent beds PB-13, PB-14 and PB-15. Polishing bed adsorbent beds PB-13, PB-14 and PB-15 are arranged in serial fluid communication wherein the portion of the section B zone 2 effluent stream in line 250 is combined with the extract stream is introduced to the top of polishing bed adsorbent bed PB-11 and a first section B zone 2 effluent from polishing bed adsorbent bed PB-11 is withdrawn from the bottom of adsorbent bed PB-11 and passed in line 234 to the top of polishing bed adsorbent bed PB-12. A second section B zone 2 effluent stream in line 250 is withdrawn from the bottom of polishing bed adsorbent bed PB-12 and passed to the top of polishing bed adsorbent bed PB-13. The section B zone 2 effluent stream in line 250 is admixed with a portion of the second swing bed extract stream, or polishing bed zone feed stream introduced via lines 222 and 254 to provide a feed mixture in line 256 which is passed to the top of section B, zone 3. Section B zone 3 comprises polishing bed adsorbent beds PB-13, PB-14 and PB-15 which are in serial fluid communication wherein feed mixture in line 256 is passed to the top of polishing bed adsorbent bed PB-13, and an intermediate section B zone 3 stream is withdrawn from the bottom of polishing bed adsorbent bed PB-13 in line 256, and passed to the top of polishing bed adsorbent bed PB-14. A second intermediate section B zone 3 stream is withdrawn from the bottom of polishing bed adsorbent bed PB-14 in line 258, and passed to the top of polishing bed adsorbent bed PB-15. A polishing bed raffinate stream in line 260 is withdrawn from polishing bed adsorbent bed PB-15 and is combined with section A zone 2 raffinate in line 232 to provide a total polishing bed raffinate stream in line 262. At the completion of each cycle, the rotary valve is sequenced to increment each polishing bed adsorbent bed by one position to the left in a counterclockwise manner, whereby PB-2 is moved to the position of PB-1, and so on, and PB-1 is moved to the position previously occupied by the last bed in the polishing bed SMB system, PB-15. At least a portion of the pooled extract stream the surge tank E-200 is withdrawn to provide the polishing bed extract stream or purified steviol glycoside stream in line 210. The polishing bed raffinate stream in line 262 is considered a fourth waste water stream and is passed to waste water treatment (not shown) for recovery of water.

In one embodiment, in the polishing bed zone, the plurality of polishing bed adsorbent beds is disposed in one or more clockwise, sequentially disposed sections. Each section has a desorption zone, a separation zone and a loading zone. In the operation of each section of the polishing bed zone; a portion of the third mobile phase desorbent is passed to the desorption zone to provide a portion of the polishing bed extract stream; a portion of the polishing bed extract stream is passed to the separation zone to provide a separation zone effluent stream; and, a portion of the polishing bed extract stream is admixed with the second swing bed elute stream to provide a portion of the polishing bed raffinate stream. At the completion of each of step of a polishing bed SMB cycle, a rotary valve is sequenced to increment each polishing bed adsorbent bed by one position to the left in a counterclockwise manner.

The following examples are provided to illustrate the present invention. These examples are shown for illustrative purposes, and any invention embodied therein should not be limited thereto.

EXAMPLES

Example 1—First Swing Bed Simulated Moving Bed Zone

The removal of a portion of the impurities, such as tri-terpenes, sterols, flavonoids and some of the pigments, from the filtered crude extract stream was demonstrated in an SMB unit in a configuration operating as the first swing bed simulated moving bed zone. A lab scale SMB unit (OCTAVE-300 unit, available from Semba Biosciences, Inc. Madison, Wis.) was used for separation of steviol glycosides from impurities including: tri-terpenes, sterols, flavonoids, and some of the pigments. The Semba Octave-300 Chromatography System is a bench top automated liquid chromatography platform designed for preparative-scale purification of chemical and biological compounds. The Octave System carries eight column positions arranged in series and connected through a proprietary pneumatic valve array. The independently working and programmable 72-valve array contains no moving parts, occupies only 3 µl per valve, and responds within 100 ms. Fluid flow is controlled by four independent pumps. The valve switching and pump flow rates are controlled via the SembaPro Software. Five adsorbent beds, each comprising a SS316 column having an inside diameter of 50 mm and a length of 600 mm were packed with about 960 grams of DIAION HP-20 resin, styrene-divinyl benzene adsorbent resin (Available from Mitsubishi Chemical Company, Tokyo, Japan).

According to the configuration in FIG. 2, the above five adsorbent beds were disposed in an arrangement illustrated by adsorbent beds SB1-1, SB1-2, SB1-3, SB1-4 and SB1-5, representing the first section of the three section unit shown in FIG. 2. In each column set, the feed (filtered crude *stevia* extract) was loaded in Zone 3 (SB1-4 and SB1-5) via lines 10, 12, and 14. Zone 3 consisted two adsorbent beds (SB1-4 and SB1-5) connected in series. During each step, only one column in zone 3 received the feed. In Zone 3, at least a portion of the impurities from the feed (filtered crude extract stream) were removed with the effluent from Zone 3 as a raffinate stream and the steviol glycosides were retained on the adsorbent. The effluent from Zone 3 was divided into a first swing bed primary raffinate stream and a secondary first swing bed raffinate stream. The first swing bed primary raffinate stream was collected from Zone 3 during the first portion of each step in the SMB cycle, and the first swing bed secondary raffinate stream was collected during the remaining portion of each step. A switch valve controlled the effluent stream flow direction. The first swing bed secondary raffinate stream was essentially a waste stream and was continuously sent for waste disposal or waste water recovery. The first swing bed primary raffinate stream was combined with the SB1 extract (line 44) withdrawn from SB1-1 and SB1 extract withdrawn from SB1-2 (line 48) as the SB1 extract stream (line 54). The SB1 desorbent (water in line 26) was loaded on to the adsorbent beds in Zone 1 (SB1-1 and SB1-2) in parallel (lines 28 and 30). The effluent from Zone 1 is called SB1 Extract 1 (line 44) and SB1 Extract 2 (line 48) and passed to an extract tank (via header 46 and lines 50 and 52). In Zone 1, essentially all of the steviol glycosides are recovered from the adsorbent beds and following desorption with water were fully regenerated. A portion of the SB1 Extract 1 is partially loaded back into Zone 2 (via line 56). Table 2 shows the SMB operating parameters for the operation of the first swing bed simulated moving bed zone.

TABLE 2

| SMB Operating Parameters-First Swing Bed SMB | | |
|---|---|---|
| PARAMETER | VALUE | UNIT |
| Step Time | 18.0 | Minutes |
| Bath Temperature | 62 | ° C. |
| Feed Rate (line 10)* | 1.5 | L/HR |
| Desorbent (line 28) | 8.0 | L/HR |
| Desorbent (line 30) | 7.1 | L/HR |
| Zone 2 (SB1-3, line 56) | 3.4 | L/HR |

TABLE 2-continued

SMB Operating Parameters-First Swing Bed SMB

| PARAMETER | VALUE | UNIT |
|---|---|---|
| Extract (line 44) | 4.7 | L/HR |
| Extract (line 48) | 7.1 | L/HR |
| Primary Raffinate (line 68, 55) | 2.4 | L/HR |
| Secondary Raffinate (line 68, 70) | 2.4 | L/HR |

*Line numbers refer to FIG. 2

The desorbent or mobile phase was low conductivity RO (reverse osmosis) water (20-50 micro Siemens). The adsorbent beds were arranged in a water bath having a temperature range of 55-70° C., and was maintained at an average bath temperature of ranging from 62-65° C. Analysis of the feed and products was carried out by high performance liquid chromatography. The samples were analyzed on a 3 μm, OROSIL C18, a reverse phase C18 column having an interior diameter of 4.6 mm and a length of 150 mm (Available from Orochem Technologies, Inc., Naperville, Ill.), at 40° C. using a mobile phase comprising a solution of 10 mM Sodium phosphate, a pH of 2.6, acetonitrile (69:31, v/v), and a flow rate of 0.6 ml/min. The SG3 concentration of sweet steviol glycosides in the total SB1 extract was 66 wt-% on an anhydrous basis, and the recovery of total steviol glycosides based on the feed to the First Swing Bed SMB was 90% on a weight basis (w/w).

Figure 5:
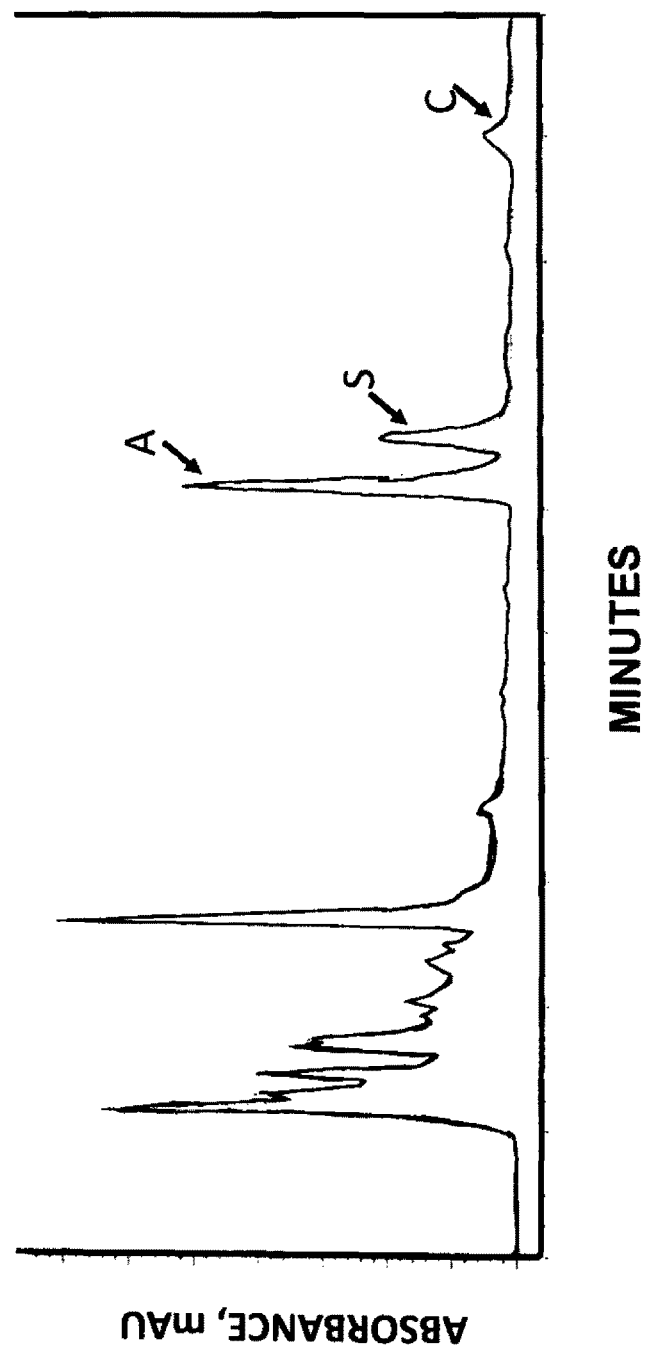
FIG. 5 is a High Performance Liquid Chromatography (HPLC) chromatographic area plot of the composition analysis of the crude *stevia* extract.
Figure 2:
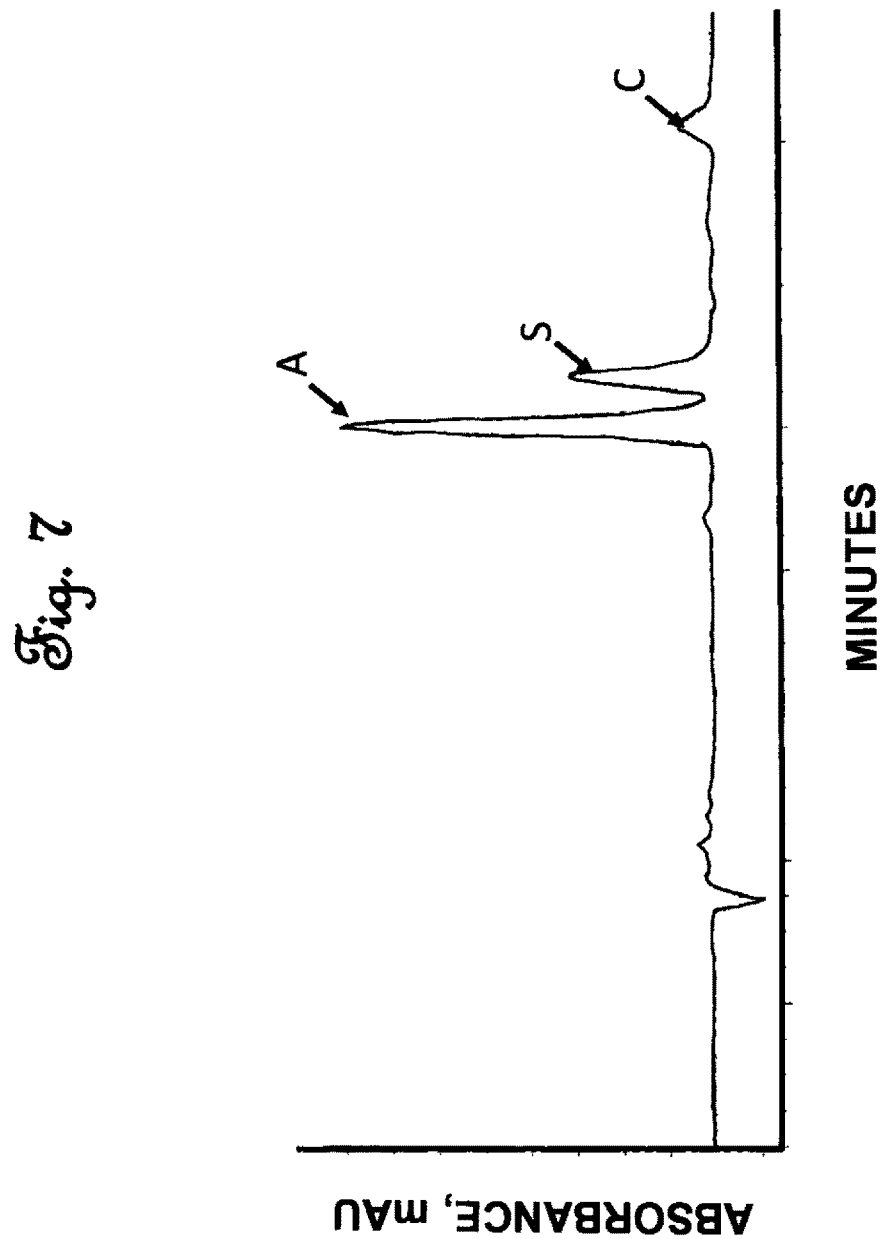

FIG. 5 is a High Performance Liquid Chromatography (HPLC) chromatographic area plot of the composition of crude *stevia* extract showing the results of a composition analysis of the crude steviol glycoside which following microfiltration with a 0.2 μm filter was the feed to the first swing bed simulated moving bed zone. The impurities appear to the left of center and the predominant sweet steviol glycosides (SG3): Rebaudioside A (A), Stevioside(S), Rebaudioside C(C) appear to the right of center.

FIG. 6 is a High Performance Liquid Chromatography (HPLC) chromatographic area plot showing the results of a composition analysis of the extract stream withdrawn from the First Swing Bed simulated moving bed zone which when compared to FIG. 5, showed the reduction of a portion of the impurities, such as tri-terpenes, sterols, flavonoids and some of the pigments, from the filtered crude extract stream.

Example 2—Second Swing Bed Simulated Moving Bed Zone

The first swing bed (SB1) extract stream withdrawn from the first swing bed simulated moving bed zone of Example 1 was concentrated by nanofiltration to provide a concentrated extract having a dry mass of about 75 g/l. The first swing bed extract stream comprises essentially all of the steviol glycosides in the crude steviol plant extract, nonionic impurities, and ionic impurities such as salts and proteins. The second swing bed employed alternating cationic and anionic resin zones to separate the ionic impurities from steviol glycosides. The second swing bed (SB2) consisted of a plurality of adsorbent beds connected in series, wherein every other adsorbent bed contained a cation or an anion resin. Six chlorinated polyvinyl chloride columns, each having an inside diameter of 100 mm (4 inches) and a length of 914 mm (36 inches) were each loaded alternately in pairs with about 5600 grams of a strongly acidic cation exchange porous styrene-divinylbenzene copolymer bead resin, DIAION PK216LH (Available from Mitsubishi Chemical Company, Tokyo, Japan), or with a weakly basic anion exchange porous acrylic-divinylbenzene copolymer bead resin, RELITE RAM2 (Available from Mitsubishi Chemical Company, Tokyo, Japan) and are connected in series fluid communication as shown in FIG. 3, for SB2-5, SB2-6, SB2-7, SB2-8, SB2-9, SB2-10. The adsorbent beds were arranged in a water bath having a temperature range of 55-70° C., and was maintained at an average bath temperature of ranging from 62-65° C. The columns were first washed with DI water (2 bed volumes) and the concentrated extract having a dry mass of about 75 g/l was loaded on to the columns at a feed rate of 300 ml/min. After loading a total of 20 liters on to the columns, the feed loading was stopped. Water was then introduced via line 112 and 114 to wash the serial arrangement of adsorbent beds with DI water at a flow rate of 300 ml/min, introducing a total volume of 25 liters of water to desorb the adsorbed steviol glycosides to provide second swing bed elute stream in line 130 comprising steviol glycosides, having a steviol glycoside concentration of about 25 g/l on an anhydrous basis, and having a reduced amount of ionic impurities such as salt and proteins relative to the crude steviol extract. By the term essentially free of ionic impurities the second swing bed elute stream contains less than about 0.5 wt-% ionic impurities on an anhydrous basis. The second swing bed elute stream comprising sweet steviol glycosides had an SG3 concentration of 85 wt-% with a steviol glycoside recovery of 98 wt-% (w/w) relative to the first swing bed (SB1) extract stream.

FIG. 7 is a High Performance Liquid Chromatography (HPLC) chromatographic area plot showing the results of a composition analysis of the second extract stream withdrawn from the Second Swing Bed simulated moving bed zone which shows the further purification of the steviol glycosides, comprising sweet steviol glycosides: Rebaudioside A, Stevioside, Rebaudioside C, and nonionic impurities including fatty acids and sugars.

Example 3—Polishing Bed Simulated Moving Bed Zone

Figure 8:
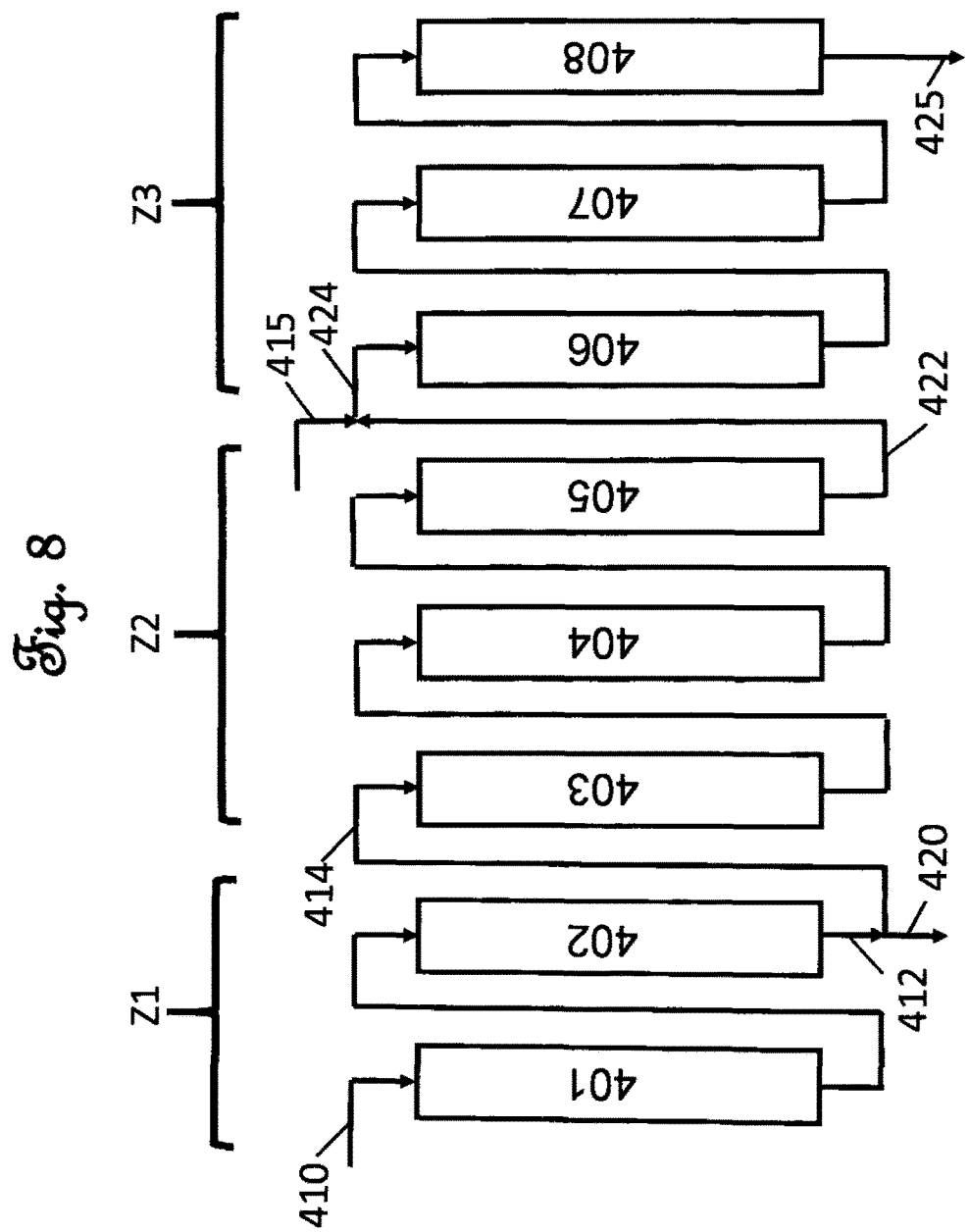
FIG. 8 is a schematic process flow diagram illustrating a configuration of the simulated moving bed cycle for a Polishing Bed system experiment which is described in Example 3.

The polishing bed zone consisted of a plurality of adsorbent beds connected in series as shown in FIG. 8. The lab scale SMB unit, OCTAVE-300 (Available from Semba Biosciences, Inc., Madison, Wis.) was employed to operate the configuration shown in FIG. 8 as a continuous simulated moving bed system. With reference to FIG. 8, adsorbent beds 401, 402, 403, 404, 405, 406, 407, and 408 were disposed in serial fluid communication such that fluid introduced at the top of any adsorbent bed n continued to the next highest adsorbent bed n+1 by passing the effluent from adsorbent bed n from the bottom of adsorbent bed n to the top of the adjacent adsorbent bed n+1. The adsorbent beds were operated in three zones, zone 1 (Z1), zone 2 (Z2), and zone 3 (Z3), whereby the elute stream from the second swing bed was loaded on to zone 3 (Z3) by introducing the second swing bed elute via lines 415 and 424 to adsorbent bed 406. In zone 3 (Z3), steviol glycosides were adsorbed in adsorbent beds 406, 407 and 408, and a polishing bed raffinate steam was withdrawn in line 425 from adsorbent bed 408. In the same step, mobile phase desorbent, comprising DI water, was introduced in line 410 to zone 1 (Z1) and adsorbent bed 401, passing serially through adsorbent beds 401 and 402, and a polishing bed extract stream was withdrawn from adsorbent bed 402 via lines 412 and 420. A portion of the polishing bed extract stream in line 414 was passed to zone 2 (Z2) and introduced to the top of adsorbent bed 403, and continuing serially through adsorbent beds 403, 404 and 405. The effluent withdrawn from the bottom of adsorbent bed 405 was passed to the top of adsorbent bed 406 in line 422, and admixed with the second swing bed elute stream in line 415 before being passed to adsorbent bed 406 in line 424. In example 3, eight adsorbent bed columns constructed of polypropylene, each having an inside diameter of 2 inches and a length of 24 inches were packed with RESINDION PH-400 resin, a rigid low swelling hydrophilic polymethacrylate polymer adsorbent characterized by a highly porous structure with an particle size of 75-200 μm (Available from Mitsubishi Chemical Company, Tokyo, Japan). The eight adsorbent beds were arranged as shown in FIG. 8 and disposed in a water bath having a polishing bed temperature range of 55-70° C., averaging about 60° C. In each step of the simulated moving bed polishing bed cycle, the second swing bed elute, having a concentration of 25 g/l in water was loaded in zone 3 (Z3) as discussed hereinabove. During each step, only one column in zone 3 (Z3) received the feed. In zone 3 (Z3), at least a portion of the fatty acid and sugar impurities, such as phospholipids and saccharides, in the second swing bed elute were removed as a primary raffinate stream (line 425). The polishing bed primary raffinate stream is essentially a waste stream, and was continuously sent to waste disposal. Zone 2 (Z2) is a separation zone and in zone 2 the separation of steviol glycosides from the fatty acid and sugar impurities takes place. The desorbent (water) was loaded on to the adsorbent beds 401 and 402 in Zone 1 in series and a polishing bed extract stream was withdrawn in lines 412 and 420. The eight adsorbent beds were operated as a simulated moving bed system. Table 3 shows the SMB operating parameters for the operation of the second swing bed simulated moving bed zone.

TABLE 3

SMB Operating Parameters- Second Swing Bed SMB

| PARAMETER | VALUE | UNITS |
| --- | --- | --- |
| Step Time | 10 | Minutes |
| Bath Temperature | 60 | ° C. |
| Feed Rate (SB2 Elute) | 25.0 | ml/minute |
| Desorbent (DI Water) | 170 | ml/minute |
| Polishing Bed Extract | 64 | ml/minute |
| Polishing Bed Raffinate | 131 | ml/minute |

The polishing bed extract stream had a total steviol glycoside purity of 97 wt-% on an anhydrous basis, and the recovery of the polishing bed extract represented a total steviol glycoside recovery of 75% on a weight basis, relative to the feed to the polishing bed simulated moving bed zone. Thus, the purity of the second swing bed (SB2) elute was enhanced from an SG3 concentration of 85 wt-% of sweet steviol glycosides on an anhydrous basis, to an enhanced SG3 concentration of 97 wt-% sweet steviol glycosides on an anhydrous basis.

Figure 9:
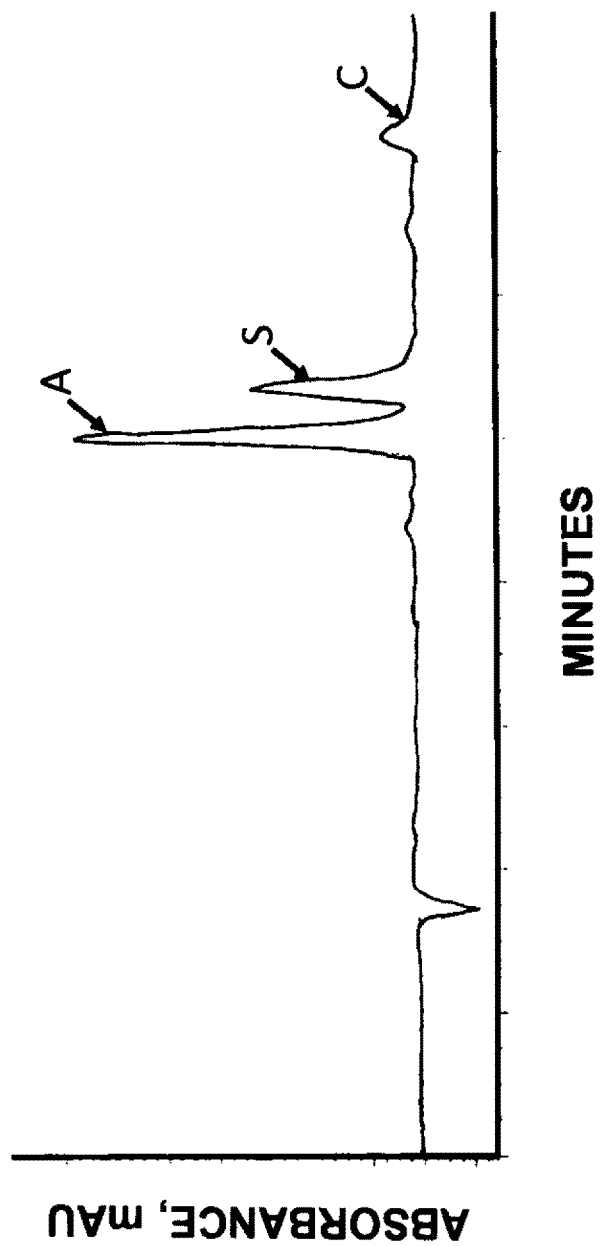
FIG. 9 is a High Performance Liquid Chromatography (HPLC) chromatographic area plot showing the results of a composition analysis of the polishing bed extract stream withdrawn from the polishing bed simulated moving bed zone of the present invention.

FIG. 9 is a High Performance Liquid Chromatography (HPLC) chromatographic area plot showing the results of a composition analysis of the polishing bed extract stream withdrawn from the polishing bed simulated moving bed zone of the present invention showing that the polishing bed extract stream essentially consists of sweet steviol glycosides (SG3): Rebaudioside A, Stevioside, and Rebaudioside C.

Example 4—Polishing Bed Simulated Moving Bed Zone

Using the same lab scale SMB unit, OCTAVE-300 (Available from Semba Biosciences, Inc., Madison, Wis.) of Example 3, the same process configuration shown in FIG. 8 was operated as a continuous simulated moving bed system as described in Example 3 for a feed which comprised 95 wt-% total steviol glycosides on an anhydrous basis. The eight adsorbent beds were operated as a simulated moving bed system Table 4 shows the SMB operating parameters for the operation of the polishing bed simulated moving bed zone.

TABLE 4

SMB Operating Parameters - Polishing Bed SMB

| PARAMETER | VALUE | UNITS |
| --- | --- | --- |
| Step Time | 6 | Minutes |
| Bath Temperature | 60 | ° C. |
| Feed Rate (Elute) | 1.0 | ml/minute |
| Desorbent (DI Water) | 25 | ml/minute |
| Polishing Bed Extract | 4.7 | ml/minute |
| Polishing Bed Raffinate | 21.3 | ml/minute |

The resulting polishing bed extract of Example 4 showed enrichment of the feed to provide a polishing bed extract stream having a total steviol glycoside purity of 98 wt-% on an anhydrous basis, and having a ratio of Rebaudioside A (A), to Stevioside (S) ranging from 2.4 to 2.5 (w/w, %) (See FIG. 10).

FIG. 10 is a High Performance Liquid Chromatography (HPLC) chromatographic area plot showing the results of a composition analysis of the enriched polishing bed extract stream having a sweet steviol glycoside concentration of 98 wt-% on an anhydrous basis.

Example 5—Overall Process Improvement of Composition

A steviol extract prepared from the extraction of *stevia* leaves using conventional hot water extraction was subjected to the continuous process of the present invention according to the process flow as shown in FIG. 1 and the operating conditions discussed hereinabove. Table 5 presents the composition of the terminal product streams of the simulated moving bed zones of the present invention and shows how the steviol glycoside purity was increased in each process step from the initial steviol glycoside purity of about 40.5% (w/w) to a final polishing bed extract purity having a sweet steviol glycoside (SG3) concentration of greater than 95 wt-% (w/w).

TABLE 5

Steviol Glycoside Composition of SMB Zone Products

| Process Stream | Rebaudioside A, % (w/w) | Stevioside % (w/w) | Rebaudioside C % (w/w) | Total % (w/w) |
| --- | --- | --- | --- | --- |
| Steviol Glycoside Extract | 28.25 | 9.25 | 3.0 | 40.50 |
| First Swing Bed Extract | 43.50 | 15.14 | 5.72 | 64.36 |
| Second Swing Bed Elute | 59.64 | 20.74 | 6.25 | 86.63 |
| Polishing Bed Extract | 62.56 | 26.09 | 6.62 | 95.27 |

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

We claim:

1. A continuous process for the purification of steviol glycosides in a crude steviol glycoside extract comprising Rebaudioside A, Rebaudioside C, stevioside, other steviol glycosides, water, tri-terpenes, sterols, flavonoids, volatile oils, pigments, gums, proteins, carotenoids, chlorophyll, vitamins, phospholipids, saccharides, solid insolubles and salts, said process comprising:

a) passing the crude steviol glycoside extract to a first filtration zone comprising a microfiltration filter having a pore size of less than about 0.2 μm to remove at least a portion of the solid insolubles to provide a filtered steviol glycoside extract;

b) passing the filtered steviol glycoside extract and a first mobile phase desorbent stream consisting of water to a first swing bed simulated moving bed zone comprising a plurality of first swing adsorbent beds containing a hydrophobic resin selective adsorbent to adsorb Rebaudioside A, Rebaudioside C, stevioside, and other steviol glycosides to provide a first swing bed extract stream comprising Rebaudioside A, Rebaudioside C, stevioside, water, and other steviol glycosides and a first group of impurities including proteins, vitamins, phospholipids, saccharides, and salts, and to provide a primary first swing bed raffinate stream comprising Rebaudioside A, Rebaudioside C, stevioside, water, and other steviol glycosides and a secondary first swing bed raffinate comprising water, tri-terpenes, sterols, flavonoids, carotenoids chlorophyll, volatile oils, pigments, and gums and combining at least a portion of the primary first swing bed raffinate with the first swing bed extract stream wherein the hydrophobic resin selective adsorbent comprises an aromatic non-polar copolymer of styrene-divinyl benzene resin;

c) passing the first swing bed extract stream to a first nanofiltration zone to remove at least a portion of water from the first swing bed extract stream to provide a first nano retentate stream and a first nano permeate stream comprising water;

d) passing the first nano retentate stream and a second mobile phase desorbent comprising water to a second swing bed simulated moving bed zone comprising a plurality of second swing adsorbent beds which are disposed in pairs wherein a first second swing adsorbent bed in each pair contains a strongly acidic cation exchange resin and a second second swing adsorbent bed in each pair contains a weakly basic anion exchange resin, said plurality of second swing adsorbent beds in the second swing bed simulated moving bed zone being divided into an adsorption/desorption zone wherein each pair of second swing adsorbent beds is disposed in serial fluid communication and a regeneration zone wherein a first pair of second swing adsorbent beds is in serial communication and a second pair of second swing adsorbent beds comprise a regeneration zone cation bed and a regeneration zone anion bed, wherein the first nano retentate stream and a second mobile phase desorbent are intermittently passed to the adsorption/desorption zone to adsorb salts, pigment and proteins from the first nano retentate stream to provide a second swing bed elute stream comprising steviol glycosides, water, phospholipids, and saccharides, and on desorption with the second mobile phase desorbent provide a second swing bed raffinate stream comprising water, proteins, pigments and salts, and the regeneration zone comprises simultaneously passing a second swing bed water wash stream to the first pair of second swing adsorbent beds in the regeneration zone and simultaneously and sequentially passing a basic wash stream, the second swing bed water wash stream, an acid wash stream, and the second swing bed water wash stream to condition the regeneration zone cation bed, and simultaneously and sequentially passing the basic wash stream and the second swing bed water wash stream to condition the regeneration zone anion bed to regenerate the regeneration zone and provide a second swing bed waste water stream which is admixed with the second swing bed raffinate stream;

e) passing the second swing bed elute stream and a third mobile phase desorbent stream comprising water to a polishing bed simulated moving bed zone, said polishing bed simulated moving bed zone comprising a plurality of polishing bed adsorbent beds containing a hydrophobic interaction resin selective for first eluting a polishing zone total raffinate stream comprising saccharides and phospholipids, and to provide a polishing bed extract stream comprising steviol glycosides, said polishing bed extract stream comprising water and an enhanced amount of steviol glycosides relative to the amount of steviol glycosides in the crude steviol glycosides;

f) passing the polishing bed extract stream to a second nanofiltration zone to remove at least a portion of water from the polishing bed extract stream to provide a second nano retentate stream and a second nano permeate stream comprising water; and, g) passing the second nano retentate stream to a drying zone to remove the water and provide a solid steviol glycoside product comprising Rebaudioside A, Rebaudioside C and Stevioside and having a sweet steviol glycoside concentration greater than about 95% (w/w) on an anhydrous basis.

2. The process of claim 1, further comprising passing the first swing bed raffinate stream, the second swing bed raffinate stream, the polishing zone total raffinate stream, the first nano permeate stream and the second nano permeate stream to a waste water recovery zone and recovering at least a portion of the water to provide at least a portion of the first, second and third mobile phase desorbent streams.

3. The process of claim 1, wherein the solid steviol glycoside product comprising Rebaudioside A, Rebaudioside C and Stevioside comprises a total steviol glycoside content greater than or equal to about 98% (w/w) on an anhydrous basis.

4. The process of claim 1, wherein the filtered crude extract stream comprises a solid content less than or equal to about 75 grams per liter.

5. The process of claim 1, wherein the first nano retentate stream comprises a solid content less than or equal to about 75 grams per liter.

6. The process of claim 1, wherein the second nano retentate stream comprises a solid content equal or less than about 150 grams per liter.

7. The process of claim 1, wherein the first nano filtration zone and the second nano filtration zone comprises a nano filter pore size of about 100 to 300 Da (Dalton).

8. The process of claim 1, wherein the process is carried out at a process operating temperature of the overall process ranging from about 60° C. to about 80° C.

9. The process of claim 1, wherein in the first swing bed simulated moving bed zone the plurality of first swing adsorbent beds comprises one or more clockwise, sequentially disposed sections each section comprising five first swing adsorbent beds, wherein a zone 1 comprises first swing adsorbent beds 1 and 2 which are desorbed with a portion of the first mobile phase desorbent to provide a portion of the first swing extract stream, a zone 2 comprising first swing adsorbent bed 3, which is loaded with a portion of the first swing bed extract stream to provide a portion of an extract recycle stream which is admixed with the filtered crude extract stream and passed to first swing adsorbent beds 4 and 5 to load the first swing adsorbent and to provide a portion of the primary first swing bed raffinate stream during a first portion of a simulated moving bed step and a portion of the secondary first swing bed raffinate stream, wherein at the completion of each of the steps of the first swing bed SMB cycle, a rotary valve is sequenced to increment each first swing adsorbent bed by one position to the left in a counterclockwise manner.

10. The process of claim 9, wherein the plurality of first swing adsorbent beds is 15 adsorbent beds and the plurality of adsorbent beds comprises 3 sections.

11. The process of claim 1, wherein in the second swing bed simulated moving bed zone the adsorption/desorption zone comprises 6 second swing adsorbent beds and the regeneration zone comprises 4 regeneration beds.

12. The process of claim 1, wherein in the polishing bed zone, the plurality of polishing bed adsorbent beds is disposed in one or more clockwise, sequentially disposed sections each section having a desorption zone, a separation zone and a loading zone, wherein a portion of the third mobile phase desorbent is passed to the desorption zone to provide a portion of the polishing bed extract stream, a portion of the polishing bed extract stream is passed to the separation zone to provide a separation zone effluent stream, and a portion of the polishing bed extract stream is admixed with the second swing bed elute stream to provide a portion of the polishing bed raffinate stream, wherein at the completion of each of step of a polishing bed SMB cycle, a rotary valve is sequenced to increment each polishing bed adsorbent bed by one position to the left in a counterclockwise manner.

13. The process of claim 1, wherein the hydrophobic resin selective adsorbent is an aromatic non-polar copolymer of styrene-divinyl benzene adsorbent resin with an effective particle size of 0.25 mm and effective surface area of 590 $m^2/g$.

14. The process of claim 1, wherein the strongly acidic cation exchange resin has an 8 percent cross-linkage with an effective particle size of about 0.5 mm.

15. The process of claim 1, wherein the weakly basic anion is a weakly basic anion exchange porous acrylic-divinylbenzene copolymer bead resin having an effective particle size of about 0.6 mm.

16. The process of claim 1, wherein the porous hydrophobic interaction resin has a particle size of 70-200 microns.

17. The process of claim 12, wherein the plurality of polishing bed adsorbent beds comprises two clockwise, sequentially disposed sections.

18. The process of claim 12, wherein each section comprises 3 polishing bed adsorbent beds in the desorption zone, 2 polishing bed adsorbent beds in the separation and at least 2 polishing bed adsorbent beds in the loading zone.

19. The process of claim 1, wherein the acid wash stream comprises an aqueous acid solution comprising HCl and having an HCl concentration of from about 2 ml HCl per 100 ml water to about 4 ml HCl per 100 ml water.

20. The process of claim 1, where in the basic wash stream comprises an aqueous basic solution comprising sodium hydroxide and having an NaOH concentration of from about 2 grams/100 ml water to about 4 grams/100 ml water.

\* \* \* \* \*